United States Patent
Simoneau et al.

(10) Patent No.: US 7,323,567 B2
(45) Date of Patent: Jan. 29, 2008

(54) RSV POLYMERASE INHIBITORS

(75) Inventors: Bruno Simoneau, Laval (CA); Josee Bordeleau, Laval (CA); Gulrez Fazal, Roxboro (CA); Serge Landry, St-Jérôme (CA); Steve Mason, Dorval (CA); Jean Rancourt, Laval (CA)

(73) Assignee: Boehringer Ingelheim (Canada) Ltd., Laval (CA)

(*) Notice: Subject to any disclaimer, the term of this patent is extended or adjusted under 35 U.S.C. 154(b) by 498 days.

(21) Appl. No.: 10/975,562

(22) Filed: Oct. 28, 2004

(65) Prior Publication Data

US 2005/0239814 A1    Oct. 27, 2005

Related U.S. Application Data

(60) Provisional application No. 60/515,820, filed on Oct. 30, 2003.

(51) Int. Cl.
C07D 471/04    (2006.01)
A61K 31/4745    (2006.01)

(52) U.S. Cl. .......................... 546/82; 546/84; 514/293
(58) Field of Classification Search .................. 546/82, 546/84; 514/293
See application file for complete search history.

(56) References Cited

U.S. PATENT DOCUMENTS 4,176,184 A    11/1979    Austel et al.

FOREIGN PATENT DOCUMENTS

| CA | 1091232 | 12/1980 |
|---|---|---|
| WO | WO99/38508 | 8/1999 |
| WO | WO 00/04900 | 2/2000 |
| WO | WO 01/00611 | 1/2001 |
| WO | WO 01/00612 | 1/2001 |
| WO | WO 01/00615 | 1/2001 |
| WO | WO 01/29054 | 4/2001 |
| WO | WO 01/95910 | 12/2001 |
| WO | WO 02/092575 | 11/2002 |

OTHER PUBLICATIONS

S. Landry, Structure-Activity-Relationship and Synthetic Aspects of Homophthalimide RSV Polymerase Inhibitors, 87th Canadian Chemistry Conference & Exhibition, Organic Workshop, May 25-28, 2004, London (Ontario) Canada.

J. Bordeleau, et al., New inhibitors of Respiratory Syncitial Virus RNA-dependent RNA Polymerase, 228th, American Chemistry Society National meeting, Aug. 22-26, 2004, Philadelphia, PA, US.

Stephen W. Mason, et al., "Polyadenylation-dependent screening assay for respiratory syncytial virus RNA transcriptase activity and identification of an inhibitor", Nucleic Acids Reseach, vol. 32, No. 16, p4758, 2004.

*Primary Examiner*—Rita Desai
(74) *Attorney, Agent, or Firm*—Michael Morris; Mary-Ellen M. Devlin; David Dow

(57) ABSTRACT

Compounds or enantiomers of formula (I) or a salt thereof:

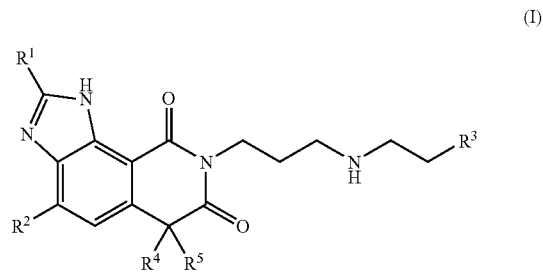

(I)

wherein $R^1$, $R^2$, $R^3$, $R^4$ and $R^5$ are as defined herein, are useful for the manufacture of a medicament for the treatment or prevention of respiratory syncytial virus infection in a mammal.

8 Claims, No Drawings

RSV POLYMERASE INHIBITORS

RELATED APPLICATIONS

This application claims benefit to U.S. provisional application No. 60/515,820 filed on Oct. 30, 2003.

FIELD OF THE INVENTION

The present invention relates to compounds, process for their synthesis, compositions and methods for the treatment or prevention of Respiratory Syncytial Virus (RSV) infection. In particular, the present invention provides novel compounds, pharmaceutical compositions containing such compounds and methods for using these compounds in the treatment or prevention of Respiratory Syncytial Virus infection.

BACKGROUND OF THE INVENTION

Respiratory Syncytial Virus (RSV) is the most common cause of severe lower respiratory tract infections (LRTI) in young infants, virtually all of whom suffer at least one RSV infection in the upper respiratory tract by the age of two. In very young infants, infection can progress to the lower respiratory tract causing bronchiolitis and pneumonia that may necessitate hospitalization.

RSV is an enveloped virus with a negative strand non-segmented RNA genome. It belongs to the Mononegavirales order, Paramyxoviridae family and *Pneumovirus* genus. RSV exhibits nucleocapsid-associated RNA dependent RNA polymerase (RdRp) activity for viral transcription and replication, which occurs in the cytoplasm of an infected cell.

The RSV polymerase is comprised of at least five viral components: the genomic RNA, and the L, N, P and M2-1 proteins. Together these components form a Ribonucleoprotein (RNP) complex with RdRp activity required for the synthesis of both viral genomic RNA ("replicase" activity) and sub-genomic mRNAs ("transcriptase" activity). As opposed to the replication of viral products, RSV mRNAs are co-transcriptionally capped (i.e. guanylated and methylated) at their 5' ends and polyadenylated at their 3' ends by the RNP complex. These modifications are necessary for translation of the viral mRNAs by the host protein synthesis machinery. The RNP complex functions exclusively in the cytoplasm of the RSV-infected cells. Since the host proteins responsible for capping of mRNAs are located in the nucleus of the cell, capping of its mRNAs by the viral RNP complex is essential for the synthesis of RSV proteins. Thus, the RSV RNP complex is an attractive target in screening for potential antiviral therapeutics since it has multiple activities essential for viral replication.

U.S. Pat. No. 4,176,184 discloses 7,7-dimethyl-2-(2-methoxyphenyl)-5-[3-(2-(3,4-dimethoxyphenyl)ethylamino)propyl]-5H,7H-imidazo[4,5-h]isoquinoline-4,6-dione dihydrochloride (example 28) having anti-arrhythmic activity.

The present invention therefore provides novel compounds, compositions, uses and methods that inhibit Respiratory Syncytial Virus polymerase essential for viral replication.

SUMMARY OF THE INVENTION

In a first aspect, the invention provides a compound of Formula (Ia), or an enantiomer or a salt thereof:

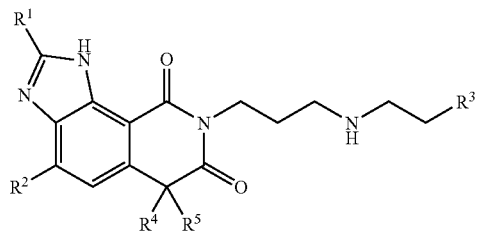

(Ia)

wherein $R^1$ is —(CH=CH)$_{0-1}$—($C_6$ or $C_{10}$)aryl or —(CH=CH)$_{0-1}$-5-, 6-, 9- or 10-membered heteroaryl, said aryl or heteroaryl being optionally substituted with one, two or three substituents, each independently selected from:

($C_{1-6}$)alkyl optionally substituted with amino, halo, ($C_{1-6}$) haloalkyl, hydroxy, ($C_{1-6}$)alkoxy, ($C_{1-6}$)alkylthio, nitro, azido, cyano, amino, ($C_{1-6}$)alkylamino, di(($C_{1-6}$)alkyl) amino, aryl and heteroaryl;

$R^2$ is H, ($C_{1-6}$)alkyl, hydroxy, halo, ($C_{1-6}$)haloalkyl, amino, ($C_{1-6}$)alkylamino, di(($C_{1-6}$)alkyl)amino, or ($C_{2-6}$)alkynyl;

$R^3$ is ($C_6$, $C_{10}$ or $C_{14}$)aryl or 5-, 6-, 9- or 10-membered heteroaryl, each of which being optionally substituted with one, two or three substituents, each independently selected from:

($C_{1-6}$)alkyl, halo, ($C_{1-6}$)haloalkyl, hydroxy, ($C_{1-6}$)alkoxy, ($C_{1-6}$)alkylthio, nitro, amino, ($C_{1-6}$)alkylamino, di (($C_{1-6}$)alkyl)amino and COO($C_{1-6}$)alkyl; and $R^4$ and $R^5$ are each independently H or ($C_{1-6}$)alkyl; or $R^4$ and $R^5$ are linked, together with the carbon atom to which they are attached, to form a ($C_{3-7}$)cycloalkyl group; with the proviso that $R^1$ is not 2-methoxyphenyl, when $R^2$ is H, $R^3$ is 3,4-dimethoxyphenyl, $R^4$ is $CH_3$ and $R^5$ is $CH_3$.

In a second aspect, the invention provides the use of a compound of formula (I), or an enantiomer or a salt thereof:

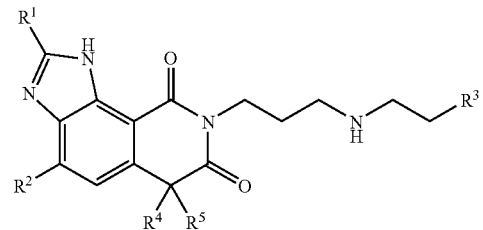

(I)

wherein $R^1$ is —(CH=CH)$_{0-1}$—($C_6$ or $C_{10}$)aryl or —(CH=CH)$_{0-1}$-5-, 6-, 9- or 10-membered heteroaryl, said aryl or heteroaryl being optionally substituted with one, two or three substituents, each independently selected from:

($C_{1-6}$)alkyl optionally substituted with amino, halo, ($C_{1-6}$) haloalkyl, hydroxy, ($C_{1-6}$)alkoxy, ($C_{1-6}$)alkylthio, nitro, azido, cyano, amino, ($C_{1-6}$)alkylamino, di(($C_{1-6}$)alkyl) amino, aryl and heteroaryl;

$R^2$ is H, ($C_{1-6}$)alkyl, hydroxy, halo, ($C_{1-6}$)haloalkyl, amino, ($C_{1-6}$)alkylamino, di(($C_{1-6}$)alkyl)amino, or ($C_{2-6}$)alkynyl;

$R^3$ is ($C_6$, $C_{10}$ or $C_{14}$)aryl or 5-, 6-, 9- or 10-membered heteroaryl, each of which being optionally substituted with one, two or three substituents, each independently selected from:

$(C_{1-6})$alkyl, halo, $(C_{1-6})$haloalkyl, hydroxy, $(C_{1-6})$alkoxy, $(C_{1-6})$alkylthio, nitro, amino, $(C_{1-6})$alkylamino, di(($C_{1-6}$)alkyl)amino and COO($C_{1-6}$)alkyl; and $R^4$ and $R^5$ are each independently H or $(C_{1-6})$alkyl; or $R^4$ and $R^5$ are linked, together with the carbon atom to which they are attached, to form a $(C_{3-7})$cycloalkyl group; in the manufacture of a medicament for the treatment or prevention of respiratory syncytial virus infection in a mammal.

In a third aspect, the invention provides a pharmaceutical composition comprising a therapeutically effective and acceptable amount of a compound of formula (I) or (Ia) in association with a pharmaceutically-acceptable carrier.

In a fourth aspect, the invention provides a pharmaceutical composition for use in the treatment or prevention of respiratory syncytial virus infection, wherein the composition comprises a therapeutically effective and acceptable amount of a compound of formula (I) or (Ia) in association with a pharmaceutically-acceptable carrier.

According to an alternate embodiment of this aspect, the pharmaceutical composition according to this invention further comprises a therapeutically effective amount of at least one other antiviral agent.

In a fifth aspect, the invention provides an anti-respiratory syncytial virus pharmaceutical composition comprising an anti-respiratory syncytial virally-effective amount of a compound of formula (I) or (Ia), alone or in combination with at least one other antiviral agent, in association with a pharmaceutically-acceptable carrier.

In a sixth aspect, the invention provides a use of a compound of formula (I) or (Ia) to inhibit the replication of a respiratory syncytial virus.

In a seventh aspect, the invention provides a use of a compound of formula (I) or (Ia), in the treatment or prevention of a respiratory syncytial virus infection in a mammal.

In an eighth aspect, the invention provides a method of treating or preventing a respiratory syncytial virus infection in a mammal comprising administering to the mammal an anti-respiratory syncytial virally-effective and acceptable amount of a compound of formula (I) or (Ia) or a composition containing such a compound, alone or in combination with at least one other antiviral agent, administered together or separately.

In a ninth aspect, the invention provides a method of inhibiting replication of a respiratory syncytial virus comprising exposing virus-infected cells to a anti-respiratory syncytial virally-effective and acceptable amount of at least one of a compound of formula (I) or (Ia).

In a tenth aspect, the invention provides a packaged pharmaceutical comprising a pharmaceutical composition containing a compound of formula (I) or (Ia) and directions identifying an administration regimen.

In an eleventh aspect, the invention provides a packaged pharmaceutical for use for the treatment or prevention of respiratory syncytial virus infection in a mammal, wherein the packaged pharmaceutical comprises a pharmaceutical composition containing a compound of formula (I) or (Ia) and directions identifying an administration regimen.

In a twelfth aspect, the invention provides an article of manufacture comprising packaging material contained within which is a composition effective to inhibit a respiratory syncytial virus, the packaging material comprising a label which indicates that the composition can be used to treat or prevent infection by a respiratory syncytial virus, wherein said composition includes a compound of formula (I) or (Ia).

DETAILED DESCRIPTION OF PREFERRED EMBODIMENTS

Definitions

As used herein, the following definitions apply unless otherwise noted: The term "halo" as used herein means a halogen radical selected from bromo, chloro, fluoro or iodo.

The term "$(C_{1-6})$alkyl" as used herein, either alone or in combination with another radical, means straight or branched-chain alkyl radicals containing up to six carbon atoms and includes, but is not limited to, methyl (Me), ethyl (Et), propyl (Pr), butyl (Bu), hexyl, 1-methylethyl (iPr), 1-methylpropyl (sec-Bu), 2-methylpropyl (iBu) and 1,1-dimethylethyl (tBu); wherein the abbreviations commonly used herein are given in parentheses.

The term "$(C_{2-6})$alkynyl" as used herein, either alone or in combination with another radical, means straight or branched-chain alkyne radicals containing from two to six carbon atoms, at least two of which are linked by a triple bond and includes, but is not limited to, —C≡CH.

The term "$(C_{3-7})$cycloalkyl" as used herein, either alone or in combination with another radical, means saturated cyclic hydrocarbon radicals containing from three to seven carbon atoms and includes cyclopropyl, cyclobutyl, cyclopentyl, cyclohexyl and cycloheptyl.

The terms "$(C_{1-6})$alkoxy" or "O—$(C_{1-6})$alkyl" as used herein interchangeably, mean a straight chain alkyl containing one to six carbon atoms linked through an oxygen atom or a branched chain alkyl radical containing three to six carbon atoms linked through an oxygen atom and includes but is not limited to methoxy, ethoxy, propoxy, 1-methylethoxy, butoxy and 1,1-dimethylethoxy. The latter radical is known commonly as tert-butoxy.

The term "$(C_{1-6})$haloalkyl" as used herein means an alkyl radical containing one to six carbon atoms wherein one or more hydrogen atoms are replaced by a halogen atom (including but not limited to trifluoromethyl).

The terms "$(C_{1-6})$alkylthio" or "S—$(C_{1-6})$alkyl" as used herein interchangeably, mean a straight chain alkyl containing one to six carbon atoms linked through a sulfur atom, or a branched chain alkyl radical containing three to six carbon atoms linked through a sulfur atom.

The term "amino" as used herein means an amino radical of formula —$NH_2$. The term "$(C_{1-6})$alkylamino" or "NH—$(C_{1-6})$alkyl" as used herein means an alkyl radical containing one to six carbon atoms linked through a nitrogen atom, and includes but is not limited to methylamino, propylamino, (1-methylethyl)amino and (2-methylbutyl)amino. The term "di(($C_{1-6}$)alkyl)amino" or "N(($C_{1-6}$)alkyl)$_2$" means an amino radical having two $(C_{1-6})$alkyl substituents, each of which contains one to six carbon atoms and includes but is not limited to dimethylamino, diethylamino, ethylmethylamino and the like.

The terms "aryl" or "($C_6$ or $C_{10}$ or $C_{14}$)aryl" used interchangeably, either alone or in combination with another radical, mean either an aromatic monocyclic system containing 6 carbon atoms or an aromatic bicyclic system containing 10 carbon atoms, or an aromatic tricyclic system containing 14 carbon atoms. For example, aryl includes but is not limited to phenyl, naphthyl or anthryl.

The terms "$(C_{7-16})$aralkyl" or "$(C_{1-6})$alkyl-aryl" used interchangeably, either alone or in combination with another radical, means an aryl as defined above linked through an alkyl group, wherein alkyl is as defined above containing from 1 to 6 carbon atoms. Aralkyl includes, but is not limited to, for example, benzyl, and phenylbutyl.

The term "Het" or "heterocycle" as used herein means a monovalent radical derived by removal of a hydrogen from a five- or six-membered, saturated or unsaturated (including aromatic) ring system containing from one to three heteroatoms each independently selected from nitrogen, oxygen and sulfur. Optionally, the heterocycle may bear one or two substituents; for example, N-oxido, $(C_{1-6})$alkyl, $(C_{1-3})$alkyl-phenyl, $(C_{1-6})$alkoxy, halo, amino or $(C_{1-6})$alkylamino. Again optionally, the five- or six-membered heterocycle can be fused to a second cycloalkyl, an aryl (e.g. phenyl) or another heterocycle.

Examples of suitable heterocycles and optionally substituted heterocycles include, but are not limited to, morpholine, thiadiazole, quinoline, isoquinoline, 3,4-methylenedioxyphenyl, benzothiazole, benzofuran, benzothiophene, pyrrolidine, tetrahydrofuran, thiazolidine, pyrrole, indole, benzimidazole, 1H-imidazole, 1-methyl-1H-imidazole, pyrazole, furan, thiophene, oxazole, isoxazole, thiazole, 2-methylthiazole, 2-aminothiazole, 2-(methylamino)thiazole, piperidine, 1-methylpiperidine, 1-methylpiperazine, 1,4-dioxane, pyridine, pyridine N-oxide, pyrimidine, 2,4-dihydroxypyrimidine, 2,4-dimethylpyrimidine, 2,6-dimethylpyridine, 1-methyl-1H-tetrazole, 2-methyl-2H-tetrazole, benzoxazole, thiazolo[4,5-b]-pyridine, heterocycles selected from the following group:

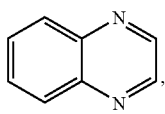 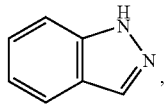

or each heterocycle exemplified in Tables 1 and 2 below.

The term "heteroaryl" as used herein means a 5- or 6-membered monocylic, or 9 or 10-membered bicyclic aromatic heterocycle as defined above. Specifically, heteroaryl includes but is not limited to: indole, benzimidazole, imidazole, furan, thiophene, oxazole, thiazole, pyrazole, pyrrole, pyridine, pyrimidine, benzofuran, benzothiophene, isoquinoline, quinoline, heteroaryl selected from the following group:

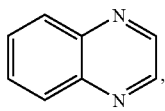 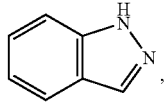

or each heteroaryl exemplified in Tables 1 and 2 below.

The term "pharmaceutically acceptable carrier" as used herein means a non-toxic, generally inert vehicle for the active ingredient which does not adversely affect the ingredient.

The term "mammal" as it is used herein is meant to encompass humans, as well as non-human mammals which are susceptible to infection by respiratory syncytial virus including domestic animals, including but not limited to cattle, pigs, horses, sheep, dogs and cats, and non-domestic animals.

The term "effective amount" means a predetermined antiviral amount of the antiviral agent, i.e. an amount of the agent sufficient to be effective against the virus in vivo. It is understood that when an antiviral agent is administered in combination with another antiviral agent, the effective amount of each antiviral agent administered in combination may be lower or higher than the effective amount of each antiviral agent administered alone. Such a situation may arise, for example, when the antiviral agents administered in combination act synergistically with each other, so that the effective amount of either or both of the antiviral agents administered in combination is lower than the effective amount of either or both of the antiviral agents administered alone. In an alternative example, the antiviral agents may act antagonistically with each other, so that the effective amount of either or both of the antiviral agents administered in combination is higher than the effective amount of either or both of the antiviral agents administered alone.

The term "salt thereof" means any acid addition salt of a compound according to the invention; preferably a pharmaceutically acceptable salt thereof.

The term "pharmaceutically acceptable salt" means a salt of a compound of formula (I) or (Ia) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts. Examples of suitable salts are found in, e.g., S. M. Birge et al., J. Pharm. Sci., 1977, 66, pp. 1-19.

The term "pharmaceutically-acceptable acid addition salt" means those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid, and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Such agents can be selected from immunomodulatory agents, inhibitors of RSV polymerase or inhibitors of another target in the RSV life cycle.

The term "immunomodulatory agent" as used herein means those agents (compounds or biologicals) that are effective to enhance or potentiate the immune system response in a mammal. Immunomodulatory agents include, for example, class I interferons (such as α-(alpha), β-(beta), δ-(delta), ω-(omega) and τ-(tau) interferons, consensus interferons and asialo-interferons), class II interferons (such as γ-(gamma) interferons) and pegylated interferons.

The term "inhibitor of RSV polymerase" as used herein means an agent (compound or biological) that is effective to inhibit the function of an RSV polymerase in a mammal.

The term "inhibitor of another target in the RSV life cycle" as used herein means an agent (compound or biological) that is effective to inhibit the formation and/or replication of RSV in a mammal other than by inhibiting the function of the RSV polymerase. This includes agents that interfere with either-host or RSV viral mechanisms necessary for the formation and/or replication of RSV in a mammal. Inhibitors of another target in the RSV life cycle include but are not limited to fusion inhibitors, including but not limited to Synagis® (palivizumab), VP14637 (ViroPharma), R170591 (Janssen), RFI-641 (BMS) or BMS-43377 (BMS); and other inhibitors including but not limited to ribavirin.

As used herein, the term "treatment" means the administration of a compound or composition according to the present invention to alleviate or eliminate symptoms of respiratory syncytial virus infection and/or to reduce or eliminate viral load in a patient and/or to reduce the incidence and/or length of time of hospitalization.

As used herein, the term "hospitalization" means medical care in a hospital, clinic or other medical facility to treat respiratory syncytial virus infection.

As used herein, the term "prevention" or "prophylaxis", used interchangeably, means the administration of a compound or composition according to the present invention pre-exposure of the individual to the virus or post-exposure of the individual to the virus but before the appearance of symptoms of the disease, and/or prior to the detection of viral infection, to prevent the appearance of symptoms of the disease.

The following sign

is used in sub-formulas to indicate the bond which is connected to the rest of the molecule as defined.

Preferred Embodiments

Compounds

According to a first embodiment, the invention provides a compound of Formula (Ia) or an enantiomer thereof or a salt thereof,

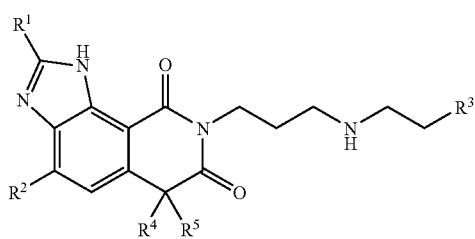

(Ia)

wherein $R^1$ is —(CH═CH)$_{0-1}$—($C_6$ or $C_{10}$)aryl or 5-, 6-, 9- or 10-membered heteroaryl, said aryl or heteroaryl being optionally substituted with one, two or three substituents, each independently selected from:

($C_{1-6}$)alkyl optionally substituted with amino, halo, ($C_{1-6}$)haloalkyl, hydroxy, ($C_{1-6}$)alkoxy, ($C_{1-6}$)alkylthio, nitro, azido, cyano, amino, ($C_{1-6}$)alkylamino, di(($C_{1-6}$)alkyl)amino, aryl and heteroaryl;

$R^2$ is H, ($C_{1-6}$)alkyl, hydroxy, halo, ($C_{1-6}$)haloalkyl, amino, ($C_{1-6}$)alkylamino, di(($C_{1-6}$)alkyl)amino, or ($C_{2-6}$)alkynyl;

$R^3$ is ($C_6$, $C_{10}$ or $C_{14}$)aryl or 5-, 6-, 9- or 10-membered heteroaryl, each of which being optionally substituted with one, two or three substituents, each independently selected from:

($C_{1-6}$)alkyl, halo, ($C_{1-6}$)haloalkyl, hydroxy, ($C_{1-6}$)alkoxy, ($C_{1-6}$)alkylthio, amino, ($C_{1-6}$)alkylamino and di(($C_{1-6}$)alkyl)amino; and $R^4$ and $R^5$ are each independently ($C_{1-6}$)alkyl; or $R^4$ and $R^5$ are linked, together with the carbon atom to which they are attached, to form a ($C_{3-7}$)cycloalkyl group; with the proviso that $R^1$ is not 2-methoxyphenyl, when $R^2$ is H, $R^3$ is 3,4-dimethoxyphenyl, $R^4$ is $CH_3$ and $R^5$ is $CH_3$.

Preferably, compounds of formula (Ia) are those wherein:
$R^1$ is (CH═CH)$_{0-1}$-phenyl, the phenyl being optionally substituted with one, two or three substituents, each independently selected from:
($C_{1-6}$)alkyl optionally substituted with amino, halo, ($C_{1-6}$)haloalkyl, hydroxy, ($C_{1-6}$)alkoxy, ($C_{1-6}$)alkylthio, amino, nitro, cyano, azido, ($C_{1-6}$)alkylamino, di(($C_{1-6}$)alkyl)amino, and heteroaryl;

or $R^1$ is a 5-, 6-, 9- or 10-membered heteroaryl optionally substituted with one, two or three substituents, each independently selected from nitro, ($C_{1-6}$)alkyl optionally substituted with amino, ($C_{1-6}$)haloalkyl, hydroxy, ($C_{1-6}$)alkoxy, halo, ($C_{1-6}$)alkylthio, cyano and heteroaryl;

$R^2$ is H, ($C_{1-6}$)alkyl, hydroxy, halo, amino, ($C_{1-6}$)alkylamino, or ($C_{2-6}$)alkynyl;

$R^3$ is naphthyl, anthryl, or phenyl optionally substituted with one, two or three substituents, each independently selected from:
($C_{1-6}$)alkyl, halo, ($C_{1-6}$)haloalkyl, hydroxy, ($C_{1-6}$)alkoxy, and ($C_{1-6}$)alkylthio;

or $R^3$ is a 5-, 6-, 9- or 10-membered heteroaryl optionally substituted with ($C_{1-6}$)alkyl; and $R^4$ and $R^5$ are each independently Me or Et; or $R^4$ and $R^5$ are linked, together with the carbon atom to which they are attached, to form a ($C_{3-7}$)cycloalkyl group; with the proviso that $R^1$ is not 2-methoxyphenyl, when $R^2$ is H, $R^3$ is 3,4-dimethoxyphenyl, $R^4$ is $CH_3$ and $R^5$ is $CH_3$.

More preferred are compounds of formula (Ia) wherein:
$R^1$ is phenyl, 2-pyridyl, quinolinyl or benzofuranyl, the phenyl and 2-pyridyl each being optionally substituted with one or two substituents, each independently selected from:
methyl, hydroxy, methoxy, nitro, cyano, methylthio, fluoro, 2-aminoethyl and $CF_3$;

$R^2$ is H, $NH_2$, bromo, chloro, or OH;

$R^3$ is naphthyl, or phenyl optionally substituted with one, two or three substituents, each independently selected from:
methyl, iodo, hydroxy, methoxy, ethoxy and methylthio; and $R^4$ and $R^5$ are each independently Me; or $R^4$ and $R^5$ are linked, together with the carbon atom to which they are attached, to form a cyclopentyl or cyclohexyl group; with the proviso that $R^1$ is not 2-methoxyphenyl, when $R^2$ is H, $R^3$ is 3,4-dimethoxyphenyl, $R^4$ is $CH_3$ and $R^5$ is $CH_3$.

Even more preferred are compounds of formula (Ia) wherein:
$R^1$ is phenyl, 2-pyridyl, quinolinyl or benzofuranyl, the phenyl and 2-pyridyl each being optionally substituted with one or two substituents, each independently selected from:

methyl, methoxy, fluoro, $CF_3$, nitro, cyano, and methylthio;

$R^2$ is H, $NH_2$, bromo, chloro, or OH;

$R^3$ is phenyl optionally substituted with one, two or three substituents, each independently selected from:
hydroxy, methoxy, ethoxy, methyl, iodo and methylthio; and $R^4$ and $R^5$ are each independently Me; or $R^4$ and $R^5$ are linked, together with the carbon atom to which they are attached, to form a cyclopentyl or cyclohexyl group; with the proviso that $R^1$ is not 2-methoxyphenyl, when $R^2$ is H, $R^3$ is 3,4-dimethoxyphenyl, $R^4$ is $CH_3$ and $R^5$ is $CH_3$.

Most preferred are compounds of formula (Ia) wherein:
$R^1$ is

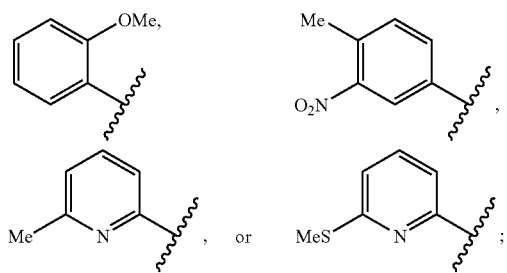

$R^2$ is $NH_2$ or bromo;

$R^3$ is phenyl substituted with one or two substituents each independently selected from hydroxy, methoxy, and iodo; and $R^4$ and $R^5$ are each independently Me; or $R^4$ and $R^5$ are linked, together with the carbon atom to which they are attached, to form a cyclohexyl group.

Specific Embodiments

Included within the scope of this invention is each single compound presented in Tables 1 and 2 below with the proviso that $R^1$ is not 2-methoxyphenyl, when $R^2$ is H, $R^3$ is 3,4-dimethoxyphenyl, $R^4$ is $CH_3$ and $R^5$ is $CH_3$.

Anti-respiratory Syncytial Virus Activity

According to a second embodiment of the present invention, compounds of the present invention are useful in the treatment or prevention of respiratory syncytial virus infections.

According to this second embodiment of the present invention, the use of compounds of the formula (I) or enantiomers thereof or salts thereof, are provided in the manufacture of a medicament for the treatment or prevention of respiratory syncytial virus infection in a mammal:

(I)

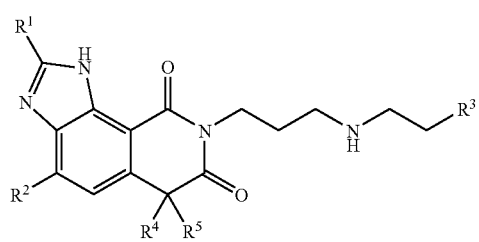

wherein $R^1$ is —$(CH=CH)_{0-1}$—$(C_6$ or $C_{10})$aryl or 5-, 6-, 9- or 10-membered heteroaryl, said aryl or heteroaryl being optionally substituted with one, two or three substituents, each independently selected from:
$(C_{1-6})$alkyl optionally substituted with amino, halo, $(C_{1-6})$haloalkyl, hydroxy, $(C_{1-6})$alkoxy, $(C_{1-6})$alkylthio, nitro, azido, cyano, amino, $(C_{1-6})$alkylamino, di$((C_{1-6})$alkyl)amino, aryl and heteroaryl;

$R^2$ is H, $(C_{1-6})$alkyl, hydroxy, halo, $(C_{1-6})$haloalkyl, amino, $(C_{1-6})$alkylamino, di$((C_{1-6})$alkyl)amino, or $(C_{2-6})$alkynyl;

$R^3$ is $(C_6, C_{10}$ or $C_{14})$aryl or 5-, 6-, 9- or 10-membered heteroaryl, each of which being optionally substituted with one, two or three substituents, each independently selected from:
$(C_{1-6})$alkyl, halo, $(C_{1-6})$haloalkyl, hydroxy, $(C_{1-6})$alkoxy, $(C_{1-6})$alkylthio, amino, $(C_{1-6})$alkylamino and di$((C_{1-6})$alkyl)amino; and $R^4$ and $R^5$ are each independently $(C_{1-6})$alkyl; or $R^4$ and $R^5$ are linked, together with the carbon atom to which they are attached, to form a $(C_{3-7})$cycloalkyl group.

Preferred is the use of compounds of formula (I) wherein:

$R^1$ is $(CH=CH)_{0-1}$-phenyl, the phenyl being optionally substituted with one, two or three substituents, each independently selected from:
$(C_{1-6})$alkyl optionally substituted with amino, halo, $(C_{1-6})$haloalkyl, hydroxy, $(C_{1-6})$alkoxy, $(C_{1-6})$alkylthio, amino, nitro, cyano, azido, $(C_{1-6})$alkylamino, di$((C_{1-6})$alkyl)amino, and heteroaryl;

or $R^1$ is a 5-, 6-, 9- or 10-membered heteroaryl optionally substituted with one, two or three substituents, each independently selected from nitro, $(C_{1-6})$alkyl optionally substituted with amino, $(C_{1-6})$haloalkyl, hydroxy, $(C_{1-6})$alkoxy, halo, $(C_{1-6})$alkylthio, cyano and heteroaryl;

$R^2$ is H, $(C_{1-6})$alkyl, hydroxy, halo, amino, $(C_{1-6})$alkylamino, or $(C_{2-4})$alkynyl;

$R^3$ is naphthyl, anthryl, or phenyl optionally substituted with one, two or three substituents, each independently selected from:
$(C_{1-6})$alkyl, halo, $(C_{1-6})$haloalkyl, hydroxy, $(C_{1-6})$alkoxy, and $(C_{1-6})$alkylthio;

or $R^3$ is a 5-, 6-, 9- or 10-membered heteroaryl optionally substituted with $(C_{1-6})$alkyl; and $R^4$ and $R^5$ are each independently Me or Et; or $R^4$ and $R^5$ are linked, together with the carbon atom to which they are attached, to form a $(C_{3-7})$cycloalkyl group.

More preferred is the use of compounds of formula (I) wherein:

$R^1$ is phenyl, 2-pyridyl, quinolinyl or benzofuranyl, the phenyl and 2-pyridyl each being optionally substituted with one or two substituents, each independently selected from:
methyl, hydroxy, methoxy, nitro, cyano, methylthio, fluoro, 2-aminoethyl and $CF_3$;

$R^2$ is H, $NH_2$, bromo, chloro, or OH;

$R^3$ is naphthyl, or phenyl optionally substituted with one, two or three substituents, each independently selected from:
methyl, iodo, hydroxy, methoxy, ethoxy and methylthio; and $R^4$ and $R^5$ are each independently Me; or $R^4$ and $R^5$ are linked, together with the carbon atom to which they are attached, to form a cyclopentyl or cyclohexyl group.

Even more preferred is the use of compounds of formula (I) wherein:
$R^1$ is phenyl, 2-pyridyl, quinolinyl or benzofuranyl, the phenyl and 2-pyridyl each being optionally substituted with one or two substituents, each independently selected from:
methyl, methoxy, fluoro, $CF_3$, nitro, cyano, and methylthio;
$R^2$ is H, $NH_2$, bromo, chloro, or OH;
$R^3$ is phenyl optionally substituted with one, two or three substituents, each independently selected from:
hydroxy, methoxy, ethoxy, methyl, iodo and methylthio; and
$R^4$ and $R^5$ are each independently Me; or $R^4$ and $R^5$ are linked, together with the carbon atom to which they are attached, to form a cyclopentyl or cyclohexyl group.

Most preferred is the use of compounds of formula (I) wherein:
$R^1$ is

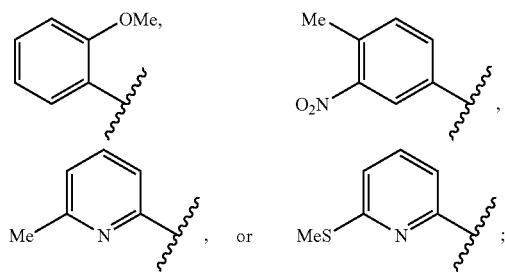

$R^2$ is $NH_2$ or bromo;
$R^3$ is phenyl substituted with one or two substituents each independently selected from hydroxy, methoxy, and iodo; and
$R^4$ and $R^5$ are each independently Me; or $R^4$ and $R^5$ are linked, together with the carbon atom to which they are attached, to form a cyclohexyl group.

Included within the scope of this invention is the use of each single compound presented in Tables 1 and 2 below for the manufacture of a medicament for the treatment or prevention of respiratory syncytial virus infection in a mammal.

According to a further embodiment the invention provides a pharmaceutical composition comprising a therapeutically effective and acceptable amount of a compound of formula (I) or (Ia) in association with a pharmaceutically-acceptable carrier.

In a further aspect, the invention provides a pharmaceutical composition for use in the treatment or prevention of respiratory syncytial virus infection, wherein the composition comprises a therapeutically effective and acceptable amount of a compound of formula (I) or (Ia), alone or in combination with at least one other antiviral agent, in association with a pharmaceutically-acceptable carrier.

According to an alternate embodiment of this aspect, the pharmaceutical compositions according to this invention may additionally comprise one or more immunomodulatory agents.

According to another alternate embodiment, the pharmaceutical compositions of this invention may additionally comprise one or more other inhibitors of RSV polymerase.

According to yet another alternate embodiment, the pharmaceutical compositions of this invention may additionally comprise one or more inhibitors of other targets in the RSV life cycle, including but not limited to, fusion inhibitors, including but not limited to Synagis® (palivizumab), VP14637 (ViroPharma), R170591 (Janssen), RFI-641 (BMS) or BMS-43377 (BMS); and other inhibitors including but not limited to ribavirin.

The pharmaceutical compositions of this invention may be administered orally, rectally, parenterally, via an implanted reservoir or topically by aerosol or nebulizer through the airways (nose or mouth). Oral or rectal administration or administration by injection is preferred. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes but is not limited to subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include but are not limited to lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Dosage levels of between about 0.01 and about 100 mg/kg body weight per day, preferably between about 0.5 and about 75 mg/kg body weight per day of the polymerase inhibitor compounds described herein are useful in a monotherapy for the prevention and treatment of RSV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of formula (I) or (Ia) and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit RSV polymerase or to treat or prevent RSV virus infection. Such treatment may also be achieved using the compounds of this invention in combination with agents which include, but are not limited to: fusion inhibitors, including but not limited to Synagis® (palivizumab), VP14637 (ViroPharma), R170591 (Janssen), RFI-641 (BMS) or BMS-43377 (BMS); and other inhibitors including but not limited to ribavirin. The additional agents may be combined with the compounds of this invention to create a single dosage form. Alternatively these additional agents may be separately administered to a mammal as part of a multiple dosage form.

Accordingly, another embodiment of this invention provides methods of inhibiting RSV polymerase activity in a mammal by administering a compound of the formula (I) or (Ia).

In a preferred embodiment, these methods are useful in decreasing RSV polymerase activity in a mammal. If the pharmaceutical composition comprises only a compound of this invention as the active component, such methods may additionally comprise the step of administering to said mammal an agent selected from an immunomodulatory agent, an antiviral agent, or another RSV polymerase inhibitor. Such additional agent may be administered to the mammal prior to, concurrently with, or following the administration of the compositions of this invention.

In an alternate preferred embodiment, these methods are useful for inhibiting viral replication in a mammal. Such methods are useful in treating or preventing RSV disease. If the pharmaceutical composition comprises only a compound of this invention as the active component, such methods may additionally comprise the step of administering to said mammal an agent selected from an immunomodulatory agent, an antiviral agent or another RSV polymerase inhibitor. Such additional agent may be administered to the mammal prior to, concurrently with, or following the administration of the composition according to this invention.

The compounds set forth herein may also be used as laboratory reagents. The compounds of this invention may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

The compounds set forth herein may also be used as research reagents. The compounds of this invention may also be used as positive control to validate cellular assays or in vitro or in vivo viral replication assays. In addition, the compounds of this invention may be used as probes in displacement assays which measure displacement of such a probe from binding to an RSV polymerase as a means for identifying inhibitors of the RSV polymerase.

Methodology

The compounds of the present invention were synthesized according to a general process as illustrated in scheme I (wherein $R^1$, $R^2$, $R^3$, $R^4$ and $R^5$ are as defined hereinbefore and $R^{1a}$, $R^{2a}$ and $R^{3a}$ are groups which may be converted to $R^1$, $R^2$ and $R^3$, respectively):

Scheme 1: General synthesis of compounds of formula (I) or (Ia)

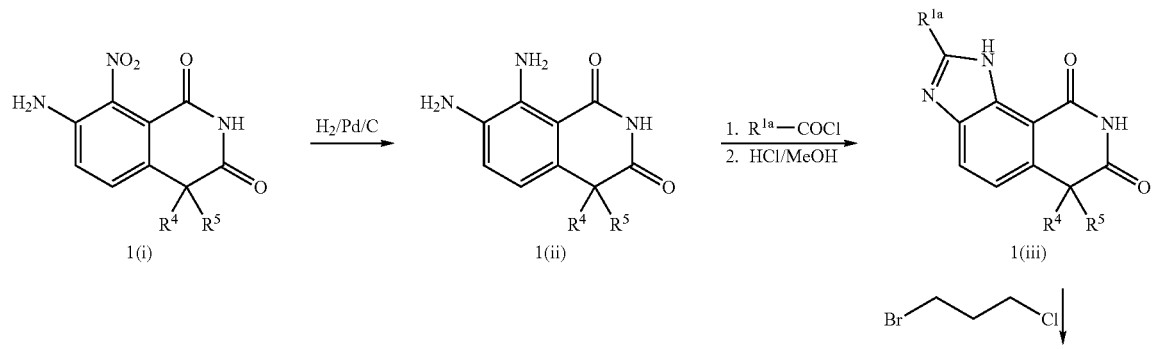

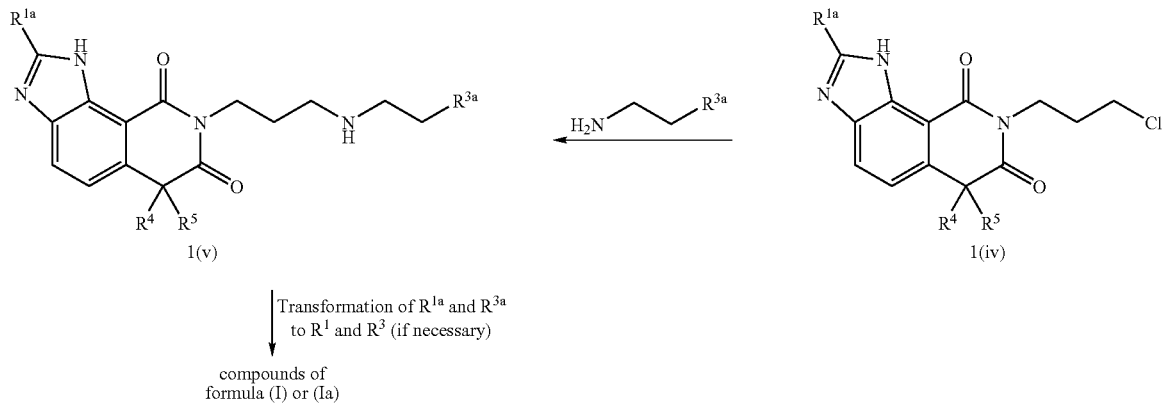

The general synthesis described in Scheme 1 is similar to the one described in U.S. Pat. No. 4,176,184. Briefly, reduction of 8-nitroisoquinoline-1,3(2H,4H)-dione 1(i) (prepared according to the procedure described in DE 3410168) to the corresponding aniline 1(ii) followed by acylation with acyl chloride and cyclization of the resulting amide gave 1H-imidazol[4,5-h]isoquinoline-7,9(6H,8H)-dione 1 (iii).

Alkylation of 1(iii) with 1-bromo-3-chloropropane gave 1(iv), which reacted with a primary amine to give 1(v). If necessary, the transformation of $R^{1a}$ and $R^{3a}$ to $R^1$ and $R^3$ by methods known to the skilled in the art (including, but not limited to, removal of protective group, alkylation, oxidation and reduction) gave the compounds of formula (I) or (Ia).

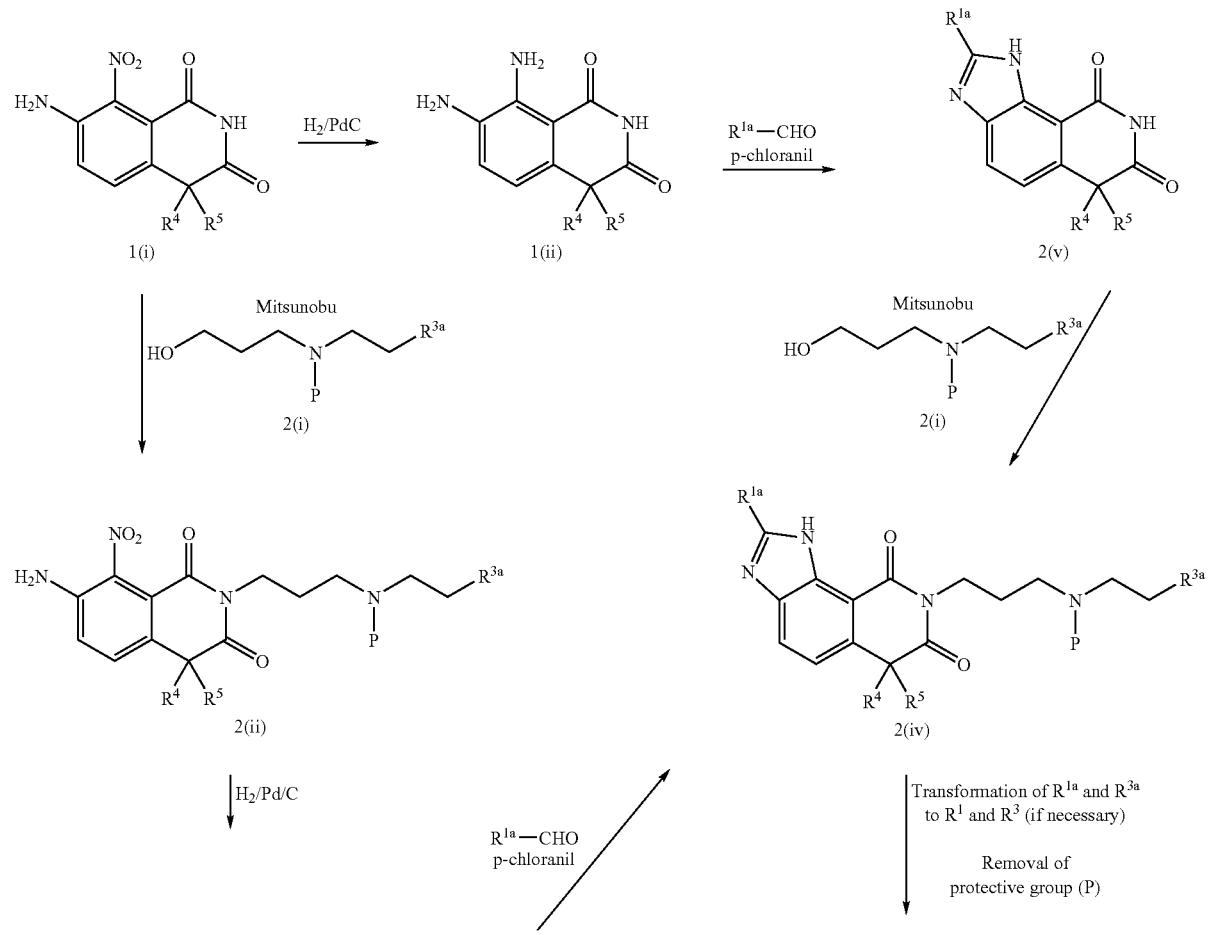

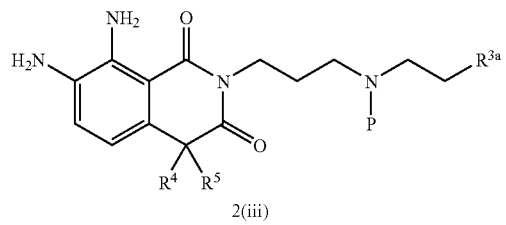

2(iii)

Alternatively, the side-chain on the isoquinoline-1,3(2H, 4H)-dione 1(i) can be incorporated using a Mitsunobu reaction with alcohol 2(i) to give 2(ii). Reduction of the nitro group on 2(ii) gave the diamino intermediate 2(iii) that was transformed to 1H-imidazol[4,5-h]isoquinoline-7,9(6H, 8H)-dione 2(iv) using an aldehyde in presence of p-chloranil. Alternative methods to generate 2(iv) from diamino 2(iii) are known to the skilled in the art. By inverting the sequence of steps, 1(ii) can be easily converted to 1H-imidazol[4,5-h]isoquinoline-7,9(6H,8H)-dione 2(v) and finally to 2(iv). Transformation of $R^{1a}$ and $R^{3a}$ to $R^1$ and $R^3$ in 2(iv) by methods known to the skilled in the art (including but not limited to removal of protective group, alkylation, oxidation and reduction), if necessary, and removal of the protective group P on the amine gave compounds of formula (I) or (Ia).

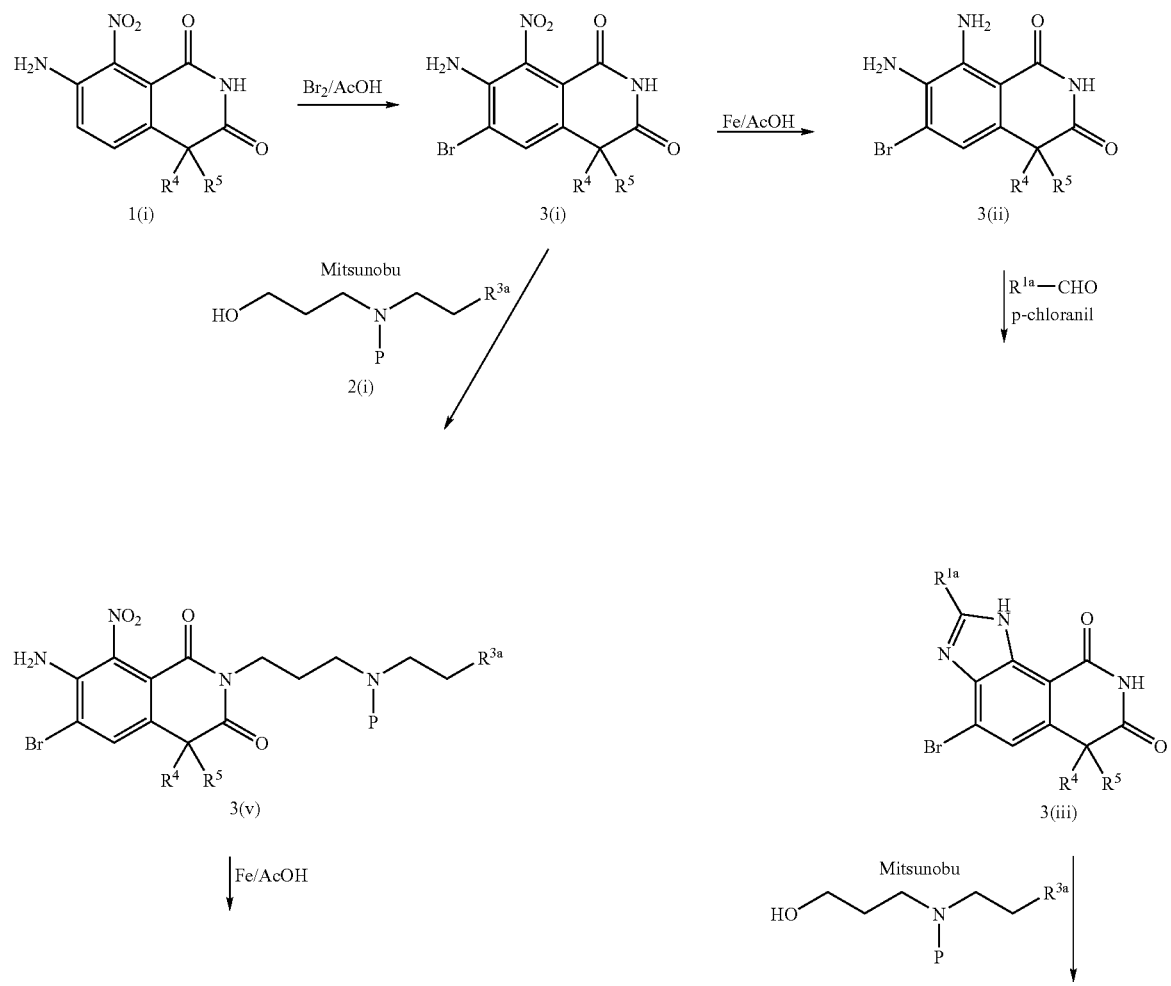

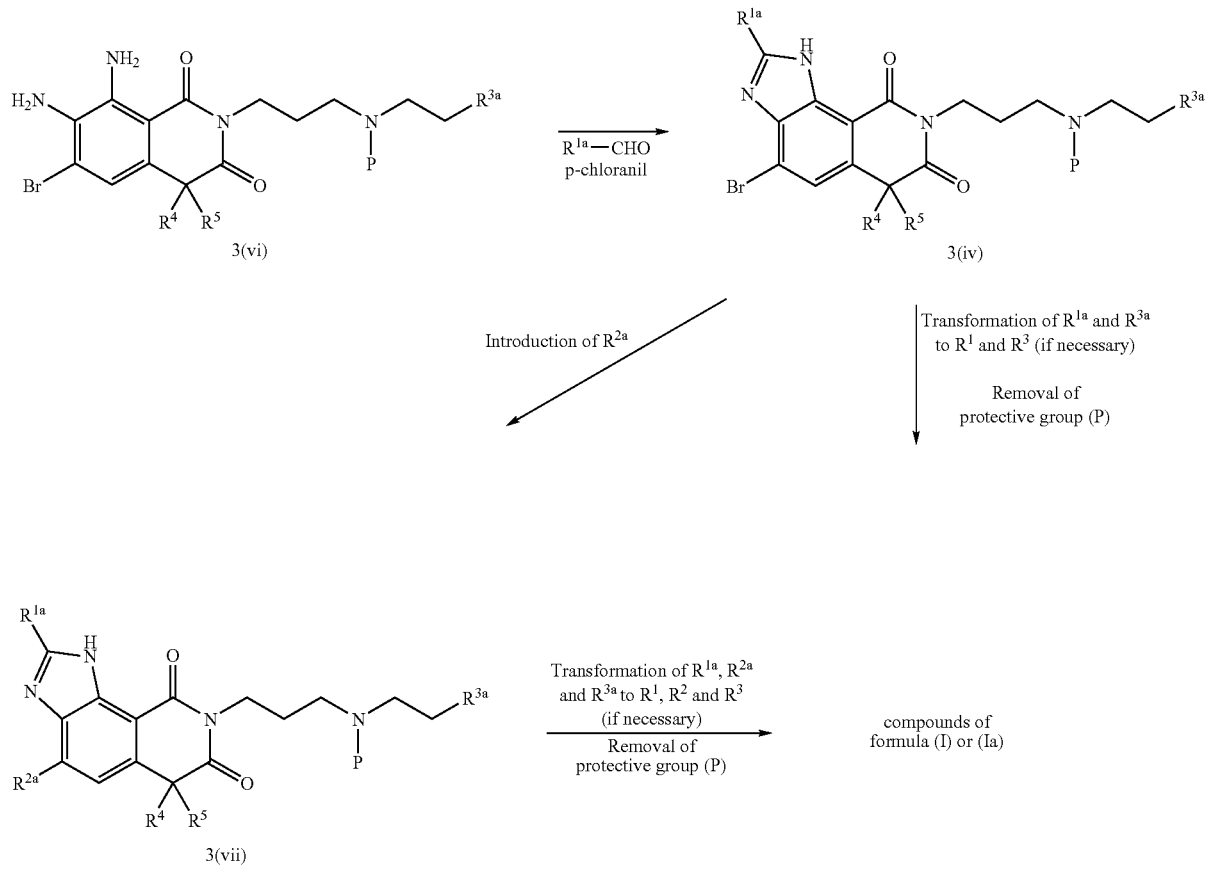

The bromination of 1(i) gave the bromo derivative 3(i), which was transformed to 3(iv) using sequences analogous to the two described in Scheme 2. 4-Bromo intermediate 3(iv) can be transformed to 3(vii) by art-recognized chemistry. Transformation of $R^{1a}$, $R^{2a}$ (if not Br) and $R^{3a}$ to $R^1$, $R^2$ and $R^3$ by methods known to the skilled in the art (including but not limited to removal of protective group, alkylation, oxidation and reduction) in 3(iv) or 3(vii), if necessary, followed by removal of the protective group P on the amine gave compounds of formula (I) or (Ia).

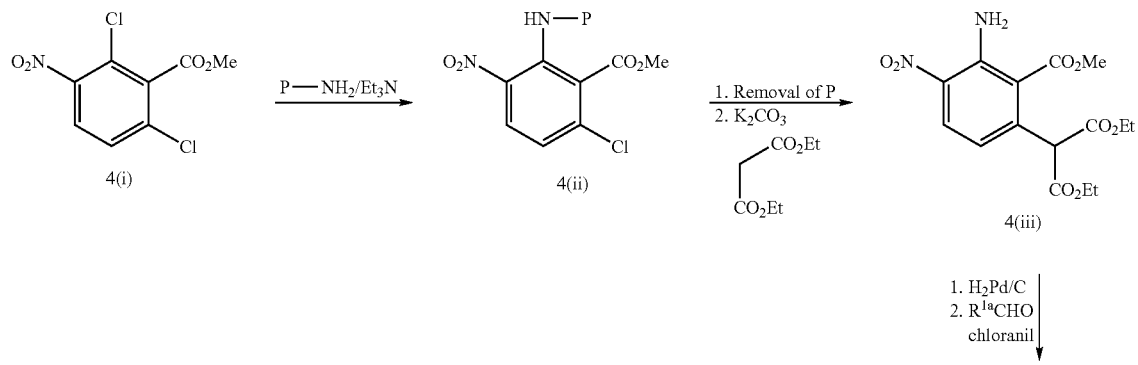

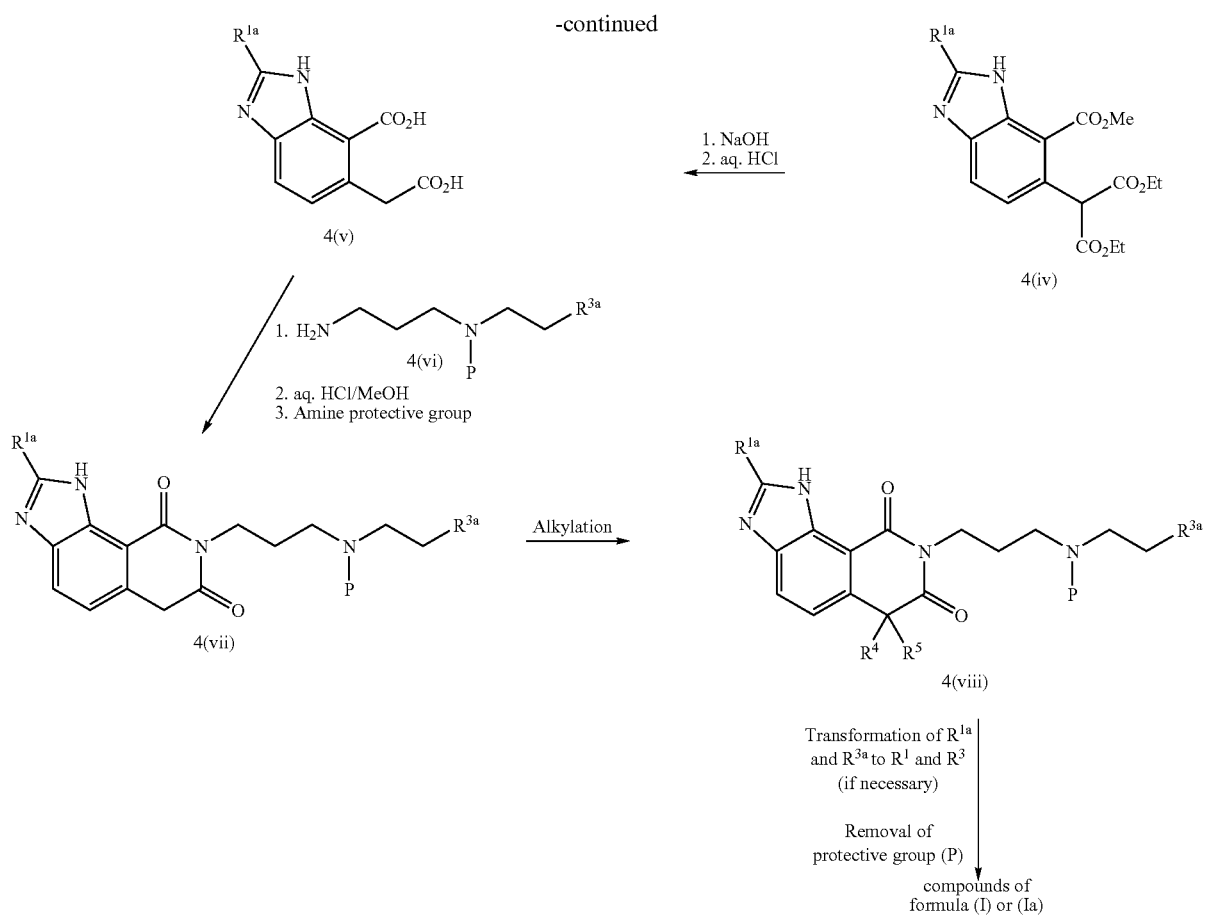

Briefly, aromatic substitution of 4(i) with a protected form of ammonia produced 4(ii). Removal of the protecting group on the aniline 4(ii) followed by a second aromatic substitution with diethyl malonate gave 4(iii). As described in previous Schemes, 4(iii) can be transformed to benzimidazole 4(iv). Upon saponification of the ester groups and decarboxylation in acidic media, diacid 4(v) was obtained. Treatment of diacid 4(v) with amine 4(vi) at high temperature gave, after acidification and protection of the amine, 4(vii). Finally, alkylation of 4(vii) followed by transformation of $R^{1a}$ and $R^{3a}$ to $R^1$ and $R^3$, if necessary, and removal of the amine protective group gave the compounds of formula (I) or (Ia).

EXAMPLES

The present invention is illustrated in further detail by the following non-limiting examples. All reactions were performed in a nitrogen or argon atmosphere unless otherwise stated. Room temperature is 18-22° C. (degrees Celsius). Solution percentages or ratios express a volume to volume relationship, unless stated otherwise.

Abbreviations or symbols used herein include:

BOC: tert-butyloxycarbonyl; dba: dibenzylideneacetone; DIAD: diisopropyl azodicarboxylate; DMF: N,N-dimethylformamide; DMSO: dimethylsulfoxide; dppf: 1,1'-bis(diphenylphosphino)ferrocene; DTT: dithiothreitol; EDTA: ethylenediaminetetraacetate; EGTA: 1,2-di(2-aminoethoxy)ethane-N,N,N',N'-tetraacetic acid; $Et_2O$: diethyl ether; EtOAc: ethyl acetate; HPLC: high performance liquid chromatography; iPr: isopropyl; Me: methyl; MeOH: methanol; MeCN: acetonitrile; Ph: phenyl; SDS: sodium dodecyl sulfate; TFA: trifluoroacetic acid; THF: tetrahydrofuran; and TrisAcetate: 2-amino-2-hydroxymethyl-1,3-propanediol acetate.

Syntheses

The following examples illustrate methods for preparing compounds of the invention.

Example 1 (Entry 1132)

8-(3-{[(3,4-dimethoxyphenyl)ethyl]amino}propyl)-6,6-dimethyl-2-(3-nitrophenyl)-1H-imidazo[4,5-h]isoquinoline-7,9(6H,8H)-dione a) tert-Butyl [3-hydroxypropyl][2-(3,4-dimethoxyphenyl)ethyl]carbamate

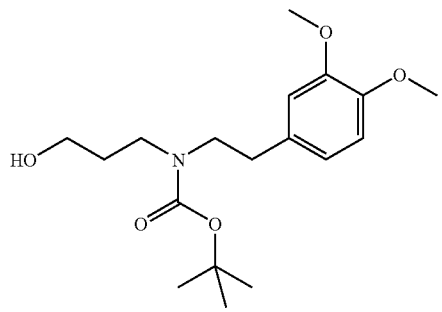

2-(3,4-Dimethoxyphenyl)ethylamine (10.0 mL, 59.3 mmol) was added to an ice-cold solution of methyl acrylate (5.40 mL, 59.3 mmol) in MeOH (60 mL). The reaction mixture was stirred at room temperature for 4 h then was concentrated under reduced pressure. Et$_3$N (10.0 mL, 71.7 mmol) and (BOC)$_2$O (14.3 g, 65.5 mmol) were added to a solution of the residue in THF (60 mL). The reaction mixture was stirred at room temperature for 1 h then was concentrated under reduced pressure. The residue was taken in Et$_2$O and the resulting solution was successively washed with aqueous 10% citric acid solution (2×), water, aqueous saturated NaHCO$_3$ solution, water (2×) and brine, dried (MgSO$_4$), filtered and concentrated under reduced pressure. LiAlH$_4$ (2.25 g, 59.3 mmol) was added to an ice-cold solution of the residue in Et$_2$O (300 mL). The reaction mixture was stirred at 0° C. for 3 h, 1 h at room temperature and then cooled to 0° C. Water (2.8 mL), 10% aqueous NaOH solution (2.8 mL) and water (8.5 mL) were successively and carefully added to the mixture. The resulting suspension was filtered and the filtrate was concentrated under reduced pressure. The residue was purified by flash chromatography (40-63μ silica gel; EtOAc:hexane, 3:2) to give the title compound (15.9 g, 79% yield).

b) tert-Butyl [3-(7-amino-4,4-dimethyl-8-nitro-1,3-dioxo-3,4-dihydro-1H-isoquinolin-2-yl)propyl]-[2-(3,4-dimethoxyphenyl)ethyl]carbamate

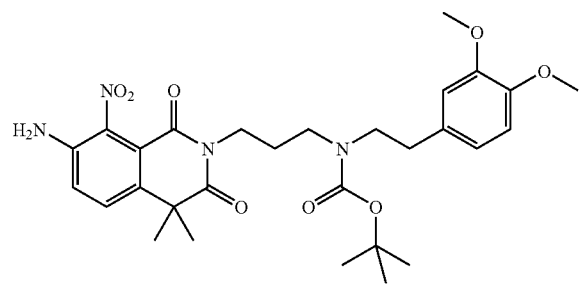

DIAD (1.92 mL, 9.75 mmol) was slowly added to an ice-cold solution of 7-amino-4,4-dimethyl-8-nitroisoquinoline-1,3(2H,4H)-dione (2.03 g, 8.14 mmol; prepared according to the method described in DE 3410168), tert-butyl [3-hydroxypropyl][2-(3,4-dimethoxyphenyl)ethyl]carbamate (3.31 g, 9.78 mmol), and PPh$_3$ (2.56 g, 9.76 mmol) in THF (40 mL). The reaction mixture was allowed to warm to room temperature and was stirred at this temperature for 16 h. The mixture was concentrated under reduced pressure and the residue was purified by flash chromatography (40-63μ silica gel, hexane:EtOAc 1:1) to give the title compound (4.29 g, 92% yield).

c) tert-Butyl [3-(7,8-diamino-4,4-dimethyl-1,3-dioxo-3,4-dihydro-1H-isoquinolin-2-yl)propyl]-[2-(3,4-dimethoxyphenyl)ethyl]carbamate

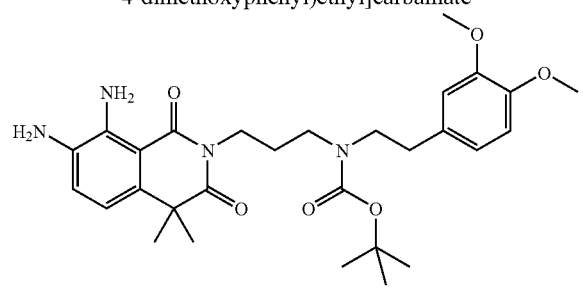

A mixture of tert-butyl [3-(7-amino-4,4-dimethyl-8-nitro-1,3-dioxo-3,4-dihydro-1H-isoquinolin-2-yl)propyl]-[2-(3,4-dimethoxyphenyl)ethyl]carbamate (3.60 g, 6.31 mmol) and 20% Pd(OH)$_2$/C (0.72 g) in EtOH (100 mL) and THF (10 mL) was stirred under H$_2$ (balloon) for 16 h. The catalyst was removed by filtration through diatomaceous earth and the filtrate was concentrated under reduced pressure. The residue was purified by flash chromatography (40-63μ silica gel, hexane:EtOAc 1:1 to 1:2) to give the title compound (2.85 g, 83% yield).

d) 8-(3-{[(3,4-dimethoxyphenyl)ethyl]amino}propyl)-6,6-dimethyl-2-(3-nitrophenyl)-1H-imidazo[4,5-h]isoquinoline-7,9(6H,8H)-dione compound 1132

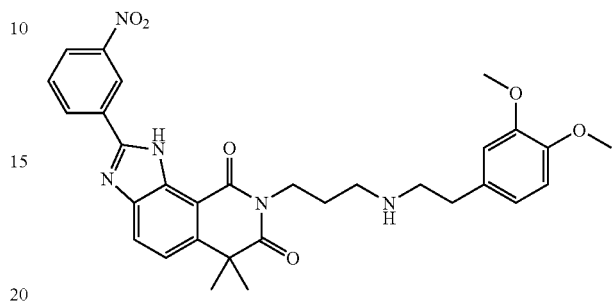

A solution of tert-butyl [3-(7,8-diamino-4,4-dimethyl-1,3-dioxo-3,4-dihydro-1H-isoquinolin-2-yl)propyl]-[2-(3,4-dimethoxyphenyl)ethyl]carbamate (25.0 mg, 46.2 μmol), 3-nitrobenzaldehyde (14.0 mg, 92.4 μmol) and p-chloranil (12.2 mg, 49.6 μmol) in MeCN (1.0 mL) was stirred at room temperature for 16 h. The reaction mixture was concentrated under reduced pressure. The residue was dissolved in CH$_2$Cl$_2$ (1.0 mL) and TFA (1.0 mL) was added. The mixture was stirred at room temperature for 1 h then was concentrated under reduced pressure. CHCl$_3$ (1 mL) and 1N aqueous NaOH solution (1 mL) were added to the residue. The aqueous layer was absorbed on a short column containing Extrelute® (~1 g). The organic phase was added after 10 min to the column. The column was washed with CHCl$_3$ and the organic solution was concentrated under reduced pressure. The residue was purified by reverse phase HPLC (CombiPrep ODS-AQ 50×20 mm, 5μ, 120 A, MeCN/water+ 0.1% TFA). The pure fractions were combined and lyophilized to give the TFA salt of compound 1132 (18.3 mg, 64% yield).

Example 2 (Entry 1059)

4-Amino-8-(3-{[(3,4-dimethoxyphenyl)ethyl]amino}propyl)-6,6-dimethyl-2-(4-methyl-3-nitrophenyl)-1H-imidazo[4,5-h]isoquinoline-7,9(6H,8H)-dione a) 7-Amino-6-bromo-4,4-dimethyl-8-nitroisoquinoline-1,3(2H,4H)-dione

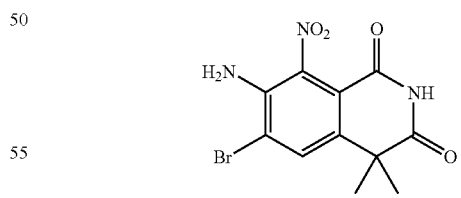

Bromine (9.27 mL, 188.6 mmol) was added dropwise to a solution of 7-amino-4,4-dimethyl-8-nitroisoquinoline-1,3(2H,4H)-dione (4.70 g, 18.86 mmol) in AcOH (190 mL). The reaction mixture was stirred at 25° C. for 2 h then was concentrated under reduced pressure. The residue was diluted with EtOAc, and successively washed with water, aqueous saturated NaHCO$_3$, aqueous saturated Na$_2$S$_2$O$_3$, and brine, dried (MgSO$_4$), filtered and concentrated under reduced pressure to give the title compound (6.10 g, 99% yield).

b) 7,8-Diamino-6-bromo-4,4-dimethylisoquinoline-1,3(2H,4H)-dione

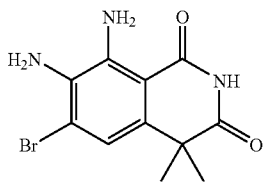

A mixture of 7-amino-6-bromo-4,4-dimethyl-8-nitroisoquinoline-1,3(2H,4H)-dione (2 g, 6.09 mmol) and iron powder (325 mesh, 2.38 g, 42.67 mmol) in AcOH (40 mL) was heated to 70° C. for 8 h. The excess iron was removed using a magnetic bar and the reaction mixture was concentrated under reduced pressure. The residue was diluted with EtOAc, and successively washed with water, aqueous saturated NaHCO$_3$, and brine, dried (MgSO$_4$), filtered and concentrated under reduced pressure to give the title compound (1.92 g, 100% yield).

c) 4-Bromo-6,6-dimethyl-2-(4-methyl-3-nitrophenyl)-1H-imidazo[4,5-h]isoquinoline-7,9(6H,8H)-dione

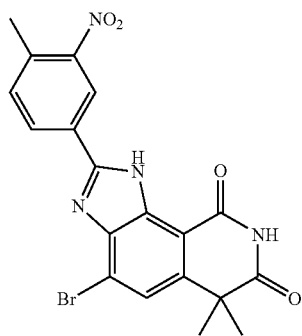

To a solution of 7,8-diamino-6-bromo-4,4-dimethylisoquinoline-1,3(2H,4H)-dione (1.40 g, 4.70 mmol) in MeCN (47 mL) and DMF (3 mL) was added 4-methyl-3-nitrobenzaldehyde (814.2 mg, 4.93 mmol) and p-chloranil (1.21 g, 4.93 mmol). The reaction mixture was stirred at 60° C. for 8 h. The cooled mixture was diluted with MeCN (50 mL) and the suspension was filtered. The solid was dried to give the title compound (1.65 g, 79% yield).

d) tert-Butyl {3-[4-bromo-6,6-dimethyl-2-(4-methyl-3-nitrophenyl)-7,9-dioxo-1,6,7,9-tetrahydro-8H-imidazo[4,5-h]isoquinolin-8-yl]propyl}[2-(3,4-dimethoxyphenyl)ethyl]carbamate

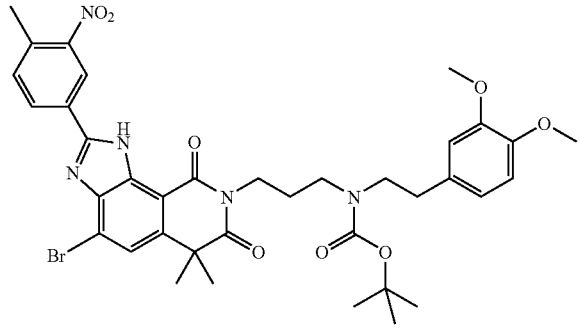

DIAD (1.15 mL, 5.87 mmol) was added dropwise to a solution of 4-bromo-6,6-dimethyl-2-(4-methyl-3-nitrophenyl)-1H-imidazo[4,5-h]isoquinoline-7,9(6H,8H)-dione (1.3 g, 2.93 mmol), tert-butyl [2-(3,4-dimethoxyphenyl)ethyl](3-hydroxypropyl)carbamate (from Example 1) (1.99 g, 5.87 mmol), and PPh$_3$ (1.54 g, 5.87 mmol) in THF (14.7 mL). The reaction mixture was stirred at 25° C. for 30 min, then was concentrated under reduced pressure. The residue was purified twice by flash chromatography (40-63µ silica gel) first with hexane:EtOAc 1:1 and then with CH$_2$Cl$_2$:acetone 95:5 to give the title compound (789.6 mg, 35% yield).

e) tert-Butyl [2-(3,4-dimethoxyphenyl)ethyl]{3-[4-[(methoxybenzyl)amino]-6,6-dimethyl-2-(4-methyl-3-nitrophenyl)-7,9-dioxo-1,6,7,9-tetrahydro-8H-imidazo[4,5-h]isoquinolin-8-yl]propyl}carbamate

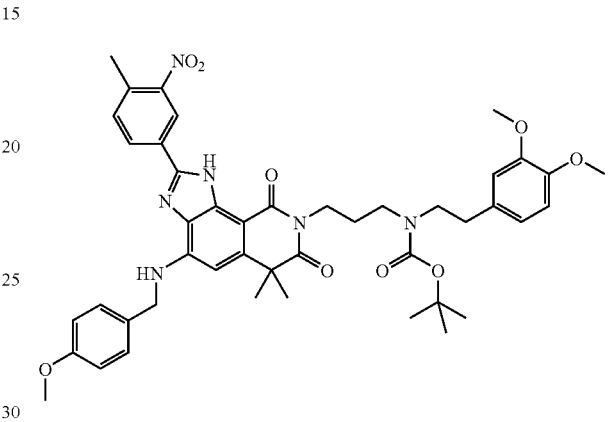

Pd$_2$(dba)$_3$ (5.6 mg, 5.12 µmol) and dppf (2.83 mg, 5.09 µmol) were added to a degassed (N$_2$ for 30 min) mixture of tert-butyl {3-[4-bromo-6,6-dimethyl-2-(4-methyl-3-nitrophenyl)-7,9-dioxo-1,6,7,9-tetrahydro-8H-imidazo[4,5-h]isoquinolin-8-yl]propyl}[2-(3,4-dimethoxyphenyl)ethyl]carbamate (780 mg, 1.02 mmol), 4-methoxybenzylamine (533 µL, 4.08 mmol) and NaOt-Bu (196 mg, 2.04 mmol) in THF (10.2 mL). The reaction mixture was stirred at 60° C. for 3 h, then was concentrated under reduced pressure. The residue was purified by flash chromatography (40-63µ silica gel; CH$_2$Cl$_2$:acetone 95:5) to give the title compound (542 mg, 65% yield).

f) 4-Amino-8-(3-{[(3,4-dimethoxyphenyl)ethyl]amino}propyl)-6,6-dimethyl-2-(4-methyl-3-nitrophenyl)-1H-imidazo[4,5-h]isoquinoline-7,9(6H,8H)-dione compound 1059

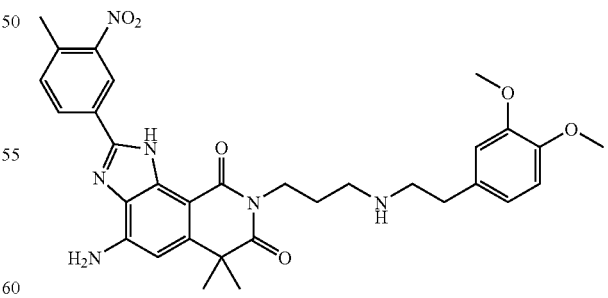

A solution of tert-butyl [2-(3,4-dimethoxyphenyl)ethyl]{3-[4-[(methoxybenzyl)amino]-6,6-dimethyl-2-(4-methyl-3-nitrophenyl)-7,9-dioxo-1,6,7,9-tetrahydro-8H-imidazo[4,5-h]isoquinolin-8-yl]propyl}carbamate (87.9 mg, 107.1 µmol) and TFA (1 mL) in CH$_2$Cl$_2$ (3 mL) was stirred at 25° C. for 45 min. The reaction mixture was concentrated under reduced pressure. The residue was purified by reverse phase HPLC (CombiPrep ODS-AQ 50×20 mm, 5μ, 120 A, MeCN/water+0.1% TFA) to give compound 1059 (36.4 mg, 56% yield).

Example 3 (Entry 2007)

8'-(3-{[2-(3,4-Dimethoxyphenyl)ethyl]amino}propyl)-2'-(2-methoxyphenyl)spiro[cyclohexane-1,6'-imidazo[4,5-h]isoquinoline]-7',9'(1'H,8'H)-dione a) Methyl 6-chloro-2-[(4-methoxybenzyl)amino]-3-nitrobenzoate

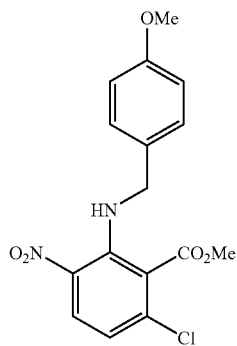

A solution of methyl 2,6-dichloro-3-nitrobenzoate (11.9 g, 47.4 mmol), p-methoxybenzylamine (8.13 g, 59.3 mmol; additional amounts of 1.63 g, 11.9 mmol added after 5 and 6.5 h), and Et₃N (7.20 g, 71.1 mmol; additional amount of 1.20 g, 11.9 mmol added after 6.5 h) in THF (190 mL) was stirred at room temperature for 15 min then was heated to reflux for 10 h. Water (100 mL) was added to the mixture and most of the THF was removed under reduced pressure. The residue was partitioned between aqueous 1 N HCl solution (350 mL) and EtOAc (500 mL). The organic layer was washed with aqueous 1 N HCl solution (100 mL) and brine (100 mL), then was dried (MgSO₄), filtered and concentrated under reduced pressure. The residue was purified by flash chromatography (10-40μ silica gel; hexane:EtOAc 6:1) to give the title compound (13.2 g, 79% yield) as a yellow solid.

b) Methyl 2-amino-6-chloro-3-nitrobenzoate

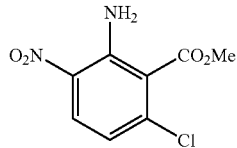

A solution of methyl 6-chloro-2-[(4-methoxybenzyl)amino]-3-nitrobenzoate (13.2 g, 37.6 mmol) and TFA (75 mL) was stirred at room temperature for 1.7 h. The mixture was diluted with EtOAc (500 mL) and water (250 mL). Solid NaHCO₃ (125 g) was slowly added to the heterogeneous mixture. Saturated aqueous NaHCO₃ solution (200 mL) and EtOAc were added and the phases were separated. The organic layer was washed with saturated aqueous NaHCO₃ solution (150 mL) and brine (50 mL) then dried (MgSO₄), filtered and concentrated under reduced pressure. The residue was purified by flash chromatography (10-40μ silica gel; hexane:EtOAc 5:1) to yield the title compound (7.03 g, 81% yield) as a yellow solid.

c) Diethyl [3-amino-2-(methoxycarbonyl)-4-nitrophenyl]malonate

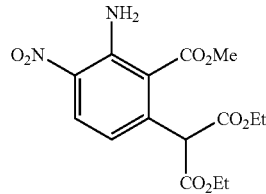

A mixture of methyl 2-amino-6-chloro-3-nitrobenzoate (4.11 g, 17.8 mmol), diethyl malonate (4.85 g, 30.3 mmol) and solid K₂CO₃ (powder, 9.11 g, 65.9 mmol) in DMF (71 mL) was heated at 60° C. for 10 h. The reaction mixture was poured into aqueous 1N HCl solution (400 mL) and the resulting solution was extracted with EtOAc (2×250 mL). The combined organic layers were washed with water (3×150 mL) and brine (100 mL), dried (MgSO₄), filtered and concentrated under reduced pressure. Purification by flash chromatography (10-40μ silica gel; hexane:EtOAc 3:1) provided the title compound (4.80 g, 76% yield) as a yellow solid.

d) Diethyl [3,4-diamino-2-(methoxycarbonyl)phenyl]malonate

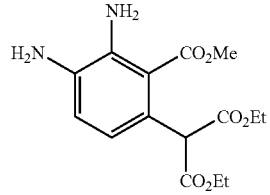

A mixture of diethyl [3-amino-2-(methoxycarbonyl)-4-nitrophenyl]malonate (4.80 g, 13.6 mmol), 10% Pd/C (0.72 g) in MeOH (70 mL) and EtOAc (70 mL) was stirred under H₂ atmosphere (balloon) at room temperature for 21 h. The catalyst was removed by filtration through diatomaceous earth. The cake was washed with EtOAc and the filtrate was concentrated to give the title compound (4.39 g, 100% yield) as a brown solid.

e) Diethyl [7-(methoxycarbonyl)-2-(2-methoxyphenyl)-1H-benzimidazol-6-yl]malonate

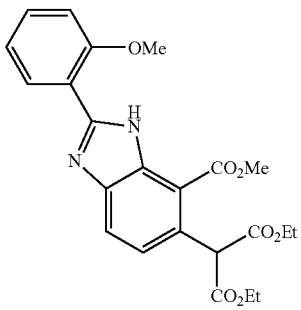

A solution of diethyl [3,4-diamino-2-(methoxycarbonyl)phenyl]malonate (4.39 g, 13.5 mmol), 2-methoxybenzaldehyde (1.97 g, 14.5 mmol) and p-chloranil (6.10 g, 14.5 mmol) in MeCN (135 mL) was stirred at room temperature for 22 h. The resulting suspension was filtered and the solid recovered was washed with MeCN (filtrate 1 kept). The solid was dissolved in EtOAc (800 mL) and the resulting solution was successively washed with aqueous 1N NaOH solution (3×150 mL), water (150 mL) and brine (100 mL), dried (MgSO₄), filtered and concentrated under reduced pressure. The resulting solid was triturated with hexane:EtOAc (1:1; 135 mL) to give the title compound (4.22 g) as a white solid (filtrate 2 kept). The filtrates 1 and 2 were combined and concentrated under reduced pressure. The residue was treated as the initial solid but the residue after washings was concentrated and purified by flash chromatography (10-40μ silica gel; hexane:EtOAc 1:1) before being triturated with hexane:EtOAc (3:2; 35 mL) to give an additional 0.72 g amount (total of 4.96 g, 83% yield) of the title compound.

f) 6-(Carboxymethyl)-2-(2-methoxyphenyl)-1H-benzimidazole-7-carboxylic acid

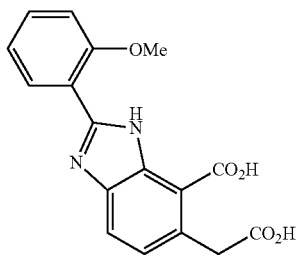

A solution of diethyl [7-(methoxycarbonyl)-2-(2-methoxyphenyl)-1H-benzimidazol-6-yl]malonate (4.96 g, 11.3 mmol) and aqueous 2 N NaOH solution (50.0 mL, 100 mmol) in THF (112 mL) and MeOH (45 mL) was stirred at room temperature for 17 h. The mixture was concentrated under reduced pressure. The residual aqueous solution was cooled to 0° C. and aqueous 2 N HCl solution (50 mL) was slowly added (pH 4 obtained). The resulting suspension was heated at 70° C. for 15 h. The cooled suspension was filtered to give the title compound (3.72 g, 100% yield) as a white solid.

g) tert-Butyl [2-(3,4-dimethoxyphenyl)ethyl]{3-[2-(2-methoxyphenyl)-7,9-dioxo-1,6,7,9-tetrahydro-8H-imidazo[4,5-h]isoquinolin-8-yl]propyl}carbamate

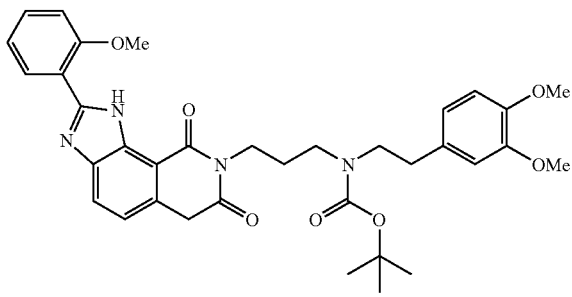

A solution of 6-(carboxymethyl)-2-(2-methoxyphenyl)-1H-benzimidazole-7-carboxylic acid (800 mg, 2.45 mmol) and tert-butyl (3-aminopropyl)[2-(3,4-dimethoxyphenyl)ethyl]carbamate (1.00 g, 2.94 mmol) in ethyleneglycol (6.1 mL) was heated at 180° C. for 1 h. The cooled mixture was dissolved in EtOAc (500 mL) and the resulting solution was washed with water (2×100 mL) and brine (200 mL), dried (MgSO₄) and concentrated under reduced pressure. A solution of the resulting yellow solid (1.04 g) and aqueous 1 N HCl solution (33 mL) in MeOH (100 mL) was heated at 70° C. for 16 h. The mixture was concentrated under reduced pressure. (BOC)₂O (1.34 g, 6.12 mmol) and Et₃N (2.06 g, 20.4 mmol) were successively added to a solution of the residue in CH₂Cl₂ (30 mL). The mixture was stirred at room temperature for 15 min then was diluted with CH₂Cl₂ (300 mL). The resulting solution was washed with water (2×100 mL) and brine (100 mL), dried (MgSO₄), filtered and concentrated under reduced pressure. The residue was purified by flash chromatography (10-40μ silica gel; hexane:EtOAc 1:2 to 1:3) to give the title compound (839 mg, 54% yield) as a yellow solid.

h) tert-Butyl [2-(3,4-dimethoxyphenyl)ethyl]{3-[2'-(2-methoxyphenyl)-7', 9'-dioxo-1',9'-dihydrospiro[cyclohexane-1,6'-imidazo[4,5-h]isoquinolin]-8'(7'H)-yl]propyl}carbamate

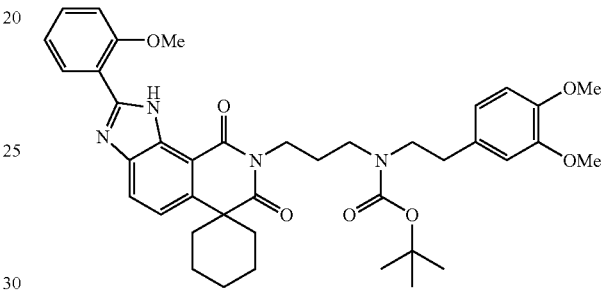

A solution of tert-butyl [2-(3,4-dimethoxyphenyl)ethyl]{3-[2-(2-methoxyphenyl)-7,9-dioxo-1,6,7,9-tetrahydro-8H-imidazo[4,5-h]isoquinolin-8-yl]propyl}carbamate (100.0 mg, 0.159 mmol), 1,3-dibromopropane (43.9 mg, 0.19 mmol) and aqueous 1 N NaOH solution (0.32 mL, 0.32 mmol) in water (1.0 mL) and EtOH (1 mL) was heated at 80° C. for 2 h. The cooled mixture was partitioned between EtOAc and water. The organic layer was washed with brine, dried (MgSO₄), filtered and concentrated under reduced pressure. The residue was purified by flash chromatography (40-63μ silica gel; hexane:EtOAc 1:1) to yield the title compound (47 mg, 43% yield) as a white foam.

i) 8'-(3-{[2-(3,4-Dimethoxyphenyl)ethyl]amino}propyl)-2'-(2-methoxyphenyl)spiro[cyclohexane-1,6'-imidazo[4,5-h]isoquinoline]-7',9'(1'H,8'H)-dione

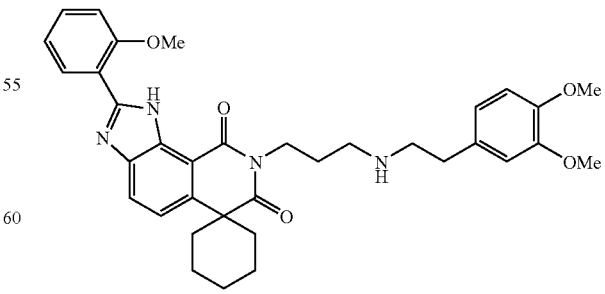

A solution of tert-butyl [2-(3,4-dimethoxyphenyl)ethyl]{3-[2'-(2-methoxyphenyl)-7', 9'-dioxo-1',9'-dihydrospiro[cyclohexane-1,6'-imidazo[4,5-h]isoquinolin]-8'(7'H)-yl]

propyl}carbamate (47.0 mg, 0.07 mmol) in 4 N HCl solution in 1,4-dioxane (3 mL) was stirred at room temperature for 1 h. The mixture was concentrated under reduced pressure and the residue was purified by reverse phase HPLC (CombiPrep ODS-AQ 50×20 mm, 5μ, 120 A, MeCN/water+0.10% TFA). The combined pure fractions were frozen and lyophilized to give the bis-trifluoroacetic acid salt of compound 2007 (51 mg, 92% yield).

Example 4

RSV Polymerase Assay

The procedure used was described by Mason, S. W. et al, *Nucleic Acids Research* (2004) 32: 4758-4767. Transcription reactions contained 0.1-1 μL RSV polymerase fraction, isolated from RSV infected HEp-2 cells using a method described previously for Newcastle Disease Virus (Hamaguchi, M., T. Yoshida, K. Nichikawa, H. Naruse & Y Nagai (1983) *Virology* 128, 105-117), in reaction buffer (50 mM TrisAcetate (pH 7.5), 120 mM potassium acetate, 4.5 mM $MgCl_2$, 5% glycerol, 2 mM EGTA, 3 mM DTT, 50 μg/ml BSA, 0.4 mM of each ATP, GTP and UTP, 4% DMSO). Reactions also contained 1 μCi $^3$H-CTP (~20 Ci/mmol). Reactions were assembled in 96-well FlashPlate™ (PerkinElmer) to which 0.6 pmol oligo-$dT_{30}$ was previously immobilized in 10 mM TrisHCl (pH 7.5) 1 mM EDTA. 0.5 M LiCl, 0.5% SDS, 70 mM NaCl, 2.5 mM KCl. Following 2 h incubation at 30° C., the reaction was stopped with hybridization buffer (17 mM TrisHCl (pH 7.5), 1.7 mM EDTA, 0.85 M LiCl, 0.85% SDS, 120 mM NaCl, 3.75 mM KCl) which favors hybridization of RNA with DNA oligonucleotides. The radionucleotide that was incorporated into newly synthesized RNA was detected by proximity to scintillant embedded in the wells of the plate using a TopCount™ (Beckman) multi-well plate scintillation detector. The compounds described in Tables 1 and 2 exhibited $IC_{50} \leq 5$ μM in this assay.

Example 5

RSV ELISA

The procedure used was described by Mason, S. W. et al, *Nucleic Acids Research* (2004) 32: 4758-4767. HEp-2 cells were plated at 10,000 cells per 96 well in DMEM 10% FBS for 24 h. The monolayer was infected with RSV-Long at an MOI of 0.1 pfu per cell in 50 μL DMEM 2% FBS. The virus was removed after one hour adsorption and 100 μL media, with or without compound, was added. Incubation was continued for 48 h. The monolayer was fixed with 0.063% glutaraldehyde. The plates were blocked with 1% BSA in phosphate-buffered saline (PBS) for one hour. Viral replication was detected with a monoclonal antibody directed against RSV F diluted 1/2000 in PBS 1% BSA. After 1 h incubation, the plates were washed and Sheep anti mouse HRP diluted 1/6000 was added. One hour later, the plates were washed and were developed with o-phenylenediamine dihydrochloride (OPD) for thirty min. The absorbance was read at 450 nm. Percent inhibition was calculated using SAS program for non-linear regression analysis.

Tables of Compounds

The following tables 1 and 2 list compounds representative of the invention. All compounds described in Tables 1 and 2 exhibited $IC_{50} \leq 5$ μM in the RSV polymerase assay of Example 4. In addition, many of the compounds described in Tables 1 and 2 are active in the RSV ELISA assay of Example 5. The following abbreviation is used within the present tables: MS: Mass spectrometric data.

TABLE 1

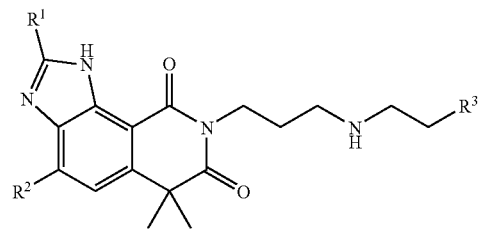

| Cpd entry # | $R^1$ | $R^2$ | $R^3$ | MS $(MH)^+$ |
|---|---|---|---|---|
| 1001 | 2-OMe-phenyl | H | 3,4-diOMe-phenyl | 557 |
| 1002 | 3-NC-phenyl | H | 3,4-diOMe-phenyl | 552 |

TABLE 1-continued

| Cpd entry # | R¹ | R² | R³ | MS (MH)⁺ |
|---|---|---|---|---|
| 1003 | 3-F-phenyl | H | 3,4-diOMe-phenyl | 595 |
| 1004 | 4-HO-phenyl | H | 3,4-diOMe-phenyl | 543 |
| 1005 | 3-F₃C-phenyl | H | 3,4-diOMe-phenyl | 595 |
| 1006 | 3-Me-phenyl | H | 3,4-diOMe-phenyl | 541 |
| 1007 | 4-Cl-3-O₂N-phenyl | H | 3,4-diOMe-phenyl | 606/608 |
| 1008 | 2-HO-3-Me-phenyl | H | 3,4-diOMe-phenyl | 557 |
| 1009 | 4-Me-3-O₂N-phenyl | H | 3,4-diOMe-phenyl | 586 |
| 1010 | 4-Cl-3-F-phenyl | H | 3,4-diOMe-phenyl | 579/581 |

TABLE 1-continued

| Cpd entry # | R¹ | R² | R³ | MS (MH)⁺ |
|---|---|---|---|---|
| 1011 | 3-Cl-C₆H₄- | H | 3,4-(OMe)₂-C₆H₃- | 561/563 |
| 1012 | 3-Cl-4-F-C₆H₃- | H | 3,4-(OMe)₂-C₆H₃- | 579/581 |
| 1013 | benzo[1,3]dioxol-4-yl | H | 3,4-(OMe)₂-C₆H₃- | 571 |
| 1014 | 4-O₂N-C₆H₄- | H | 3,4-(OMe)₂-C₆H₃- | 572 |
| 1015 | 2,3-Cl₂-C₆H₃- | H | 3,4-(OMe)₂-C₆H₃- | 595/597/599 |
| 1016 | 3,4-Me₂-C₆H₃- | H | 3,4-(OMe)₂-C₆H₃- | 555 |
| 1017 | 4-MeO-3-O₂N-C₆H₃- | H | 3,4-(OMe)₂-C₆H₃- | 602 |

TABLE 1-continued

| Cpd entry # | R¹ | R² | R³ | MS (MH)⁺ |
|---|---|---|---|---|
| 1018 | 3-F, 2-OMe phenyl | H | 3,4-diOMe phenyl | 575 |
| 1019 | 4-NMe₂, 3-NO₂ phenyl | H | 3,4-diOMe phenyl | 615 |
| 1020 | 4-OH, 3-NO₂ phenyl | H | 3,4-diOMe phenyl | 588 |
| 1021 | 3-OMe, 4-OH, 5-NO₂ phenyl | H | 3,4-diOMe phenyl | 618 |
| 1022 | 2,3-diF phenyl | H | 3,4-diOMe phenyl | 563 |
| 1023 | 2,5-diF phenyl | H | 3,4-diOMe phenyl | 563 |
| 1024 | 2,3,4-triF phenyl | H | 3,4-diOMe phenyl | 581 |
| 1025 | 4-Me, 3-F phenyl | H | 3,4-diOMe phenyl | 559 |

TABLE 1-continued
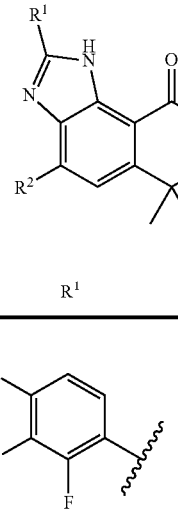
| Cpd entry # | R¹ | R² | R³ | MS (MH)⁺ |
|---|---|---|---|---|
| 1026 | 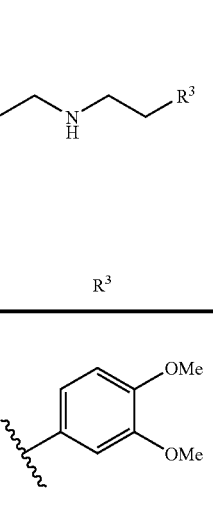 | H | 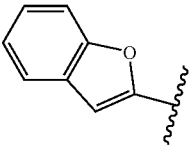 | 577 |
| 1027 | 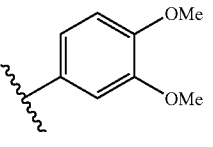 | H | 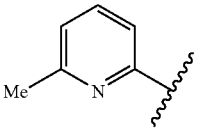 | 567 |
| 1028 | 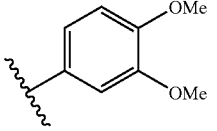 | H | 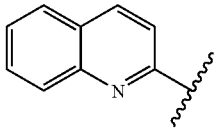 | 542 |
| 1029 | 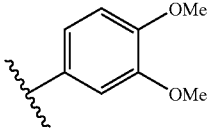 | H | 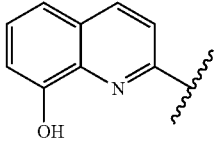 | 578 |
| 1030 | 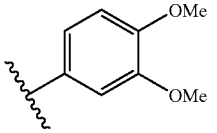 | H | 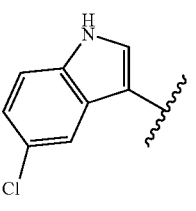 | 594 |
| 1031 | 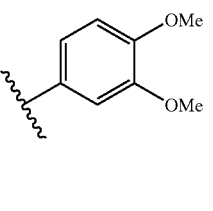 | H | 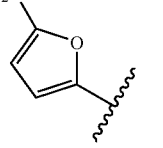 | 600/602 |
| 1032 | 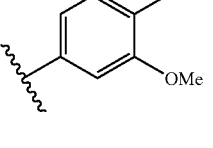 | H | | 562 |

TABLE 1-continued
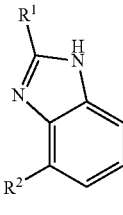
| Cpd entry # | R¹ | R² | R³ | MS (MH)⁺ |
|---|---|---|---|---|
| 1033 | 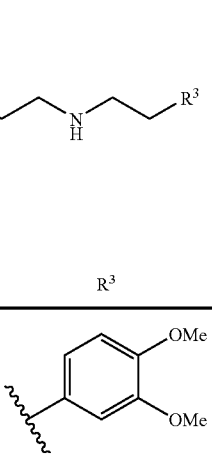 | H | 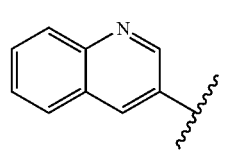 | 566 |
| 1034 | 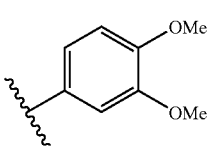 | H | 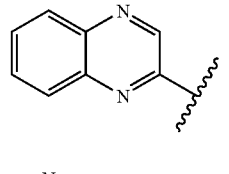 | 578 |
| 1035 | 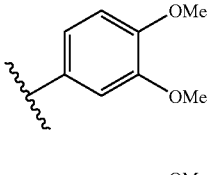 | H | 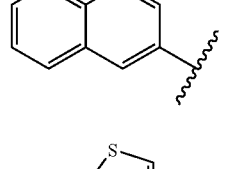 | 579 |
| 1036 | 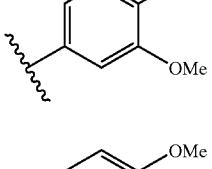 | H | 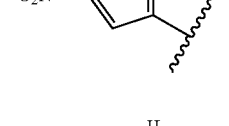 | 578 |
| 1037 | 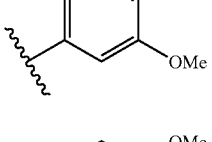 | H | 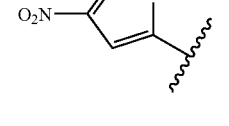 | 578 |
| 1038 | 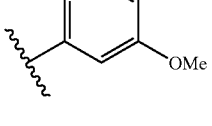 | H | 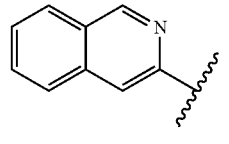 | 561 |
| 1039 | 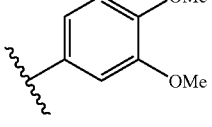 | H | 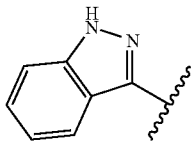 | 578 |
| 1040 | 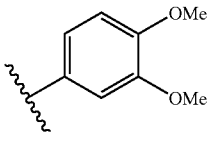 | H | | 567 |

TABLE 1-continued
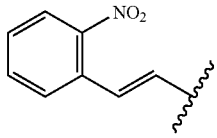
| Cpd entry # | R¹ | R² | R³ | MS (MH)⁺ |
|---|---|---|---|---|
| 1041 | 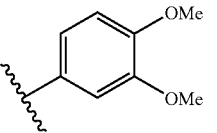 | H | 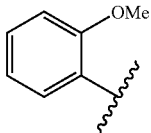 | 598 |
| 1042 | 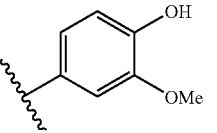 | H | 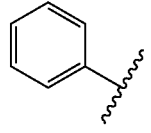 | 543 |
| 1043 | 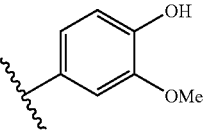 | H | 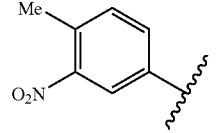 | 513 |
| 1044 | 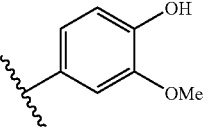 | H | 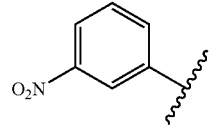 | 572 |
| 1045 | 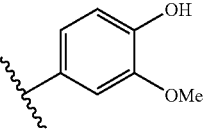 | H | 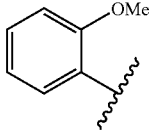 | 558 |
| 1046 | 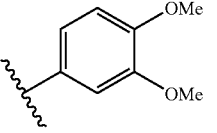 | Br | 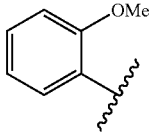 | 635/637 |
| 1047 | 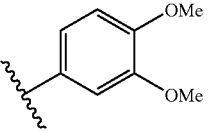 | Et | 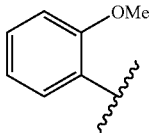 | 585 |
| 1048 | 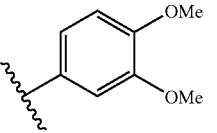 | NH₂ | | 572 |

TABLE 1-continued

| Cpd entry # | R¹ | R² | R³ | MS (MH)⁺ |
|---|---|---|---|---|
| 1049 | 2-OMe-phenyl | C≡CH | 3,4-diOMe-phenyl | 581 |
| 1050 | 2-OMe-phenyl | NHMe | 3,4-diOMe-phenyl | 586 |
| 1051 | 2-OMe-phenyl | Me | 3,4-diOMe-phenyl | 571 |
| 1052 | phenyl | Br | 3,4-diOMe-phenyl | 605/607 |
| 1053 | 4-Me-3-NO₂-phenyl | Br | 3,4-diOMe-phenyl | 664/666 |
| 1054 | 4-Me-3-NO₂-phenyl | Cl | 3,4-diOMe-phenyl | 620/622 |
| 1055 | 4-Me-3-NO₂-phenyl | OH | 3,4-diOMe-phenyl | 602 |
| 1056 | 2-OMe-phenyl | Br | 4-OH-3-OMe-phenyl | 621/623 |

TABLE 1-continued

| Cpd entry # | R¹ | R² | R³ | MS (MH)⁺ |
|---|---|---|---|---|
| 1057 | 4-Me-3-NO₂-phenyl | Br | 4-OH-3-OMe-phenyl | 650/652 |
| 1058 | 4-Me-3-NO₂-phenyl | NH₂ | 4-OH-3-OMe-phenyl | 587 |
| 1059 | 4-Me-3-NO₂-phenyl | NH₂ | 3,4-diOMe-phenyl | 601 |
| 1060 | quinolin-2-yl | Br | 3,4-diOMe-phenyl | 656/658 |
| 1061 | benzofuran-2-yl | Br | 3,4-diOMe-phenyl | 645/647 |
| 1062 | 6-Me-pyridin-4-yl | Br | 3,4-diOMe-phenyl | 620/622 |
| 1063 | 3-CN-phenyl | Br | 3,4-diOMe-phenyl | 630/632 |
| 1064 | 3-Me-phenyl | Br | 3,4-diOMe-phenyl | 619/621 |

TABLE 1-continued

| Cpd entry # | R¹ | R² | R³ | MS (MH)⁺ |
|---|---|---|---|---|
| 1065 | 3-(F₃C)-phenyl | Br | 3,4-(MeO)₂-phenyl | 673/675 |
| 1066 | 3-F-phenyl | Br | 3,4-(MeO)₂-phenyl | 623/625 |
| 1067 | 3,4-diMe-phenyl | Br | 3,4-(MeO)₂-phenyl | 633/635 |
| 1068 | 2-Me-imidazol-4-yl | Br | 3,4-(MeO)₂-phenyl | 609/611 |
| 1069 | 6-MeO-pyridin-2-yl | Br | 3,4-(MeO)₂-phenyl | 636/638 |
| 1070 | 1H-indol-3-yl | Br | 3,4-(MeO)₂-phenyl | 644/646 |
| 1071 | 6-F-pyridin-2-yl | Br | 3,4-(MeO)₂-phenyl | 624/626 |
| 1072 | 6-(pyrazol-1-yl)-pyridin-2-yl | Br | 3,4-(MeO)₂-phenyl | 672/674 |

TABLE 1-continued
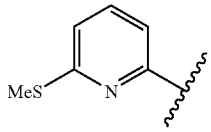
| Cpd entry # | R¹ | R² | R³ | MS (MH)⁺ |
|---|---|---|---|---|
| 1073 | 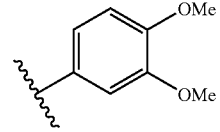 | Br | 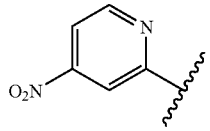 | 652/654 |
| 1074 | 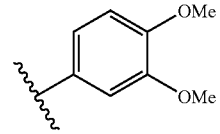 | Br | 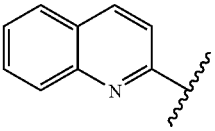 | 651/653 |
| 1075 | 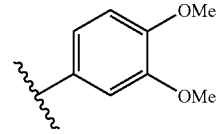 | NH₂ | 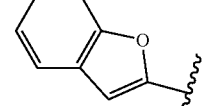 | 593 |
| 1076 | 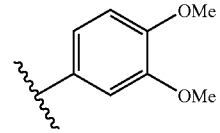 | NH₂ | 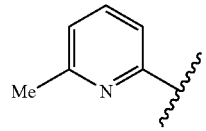 | 582 |
| 1077 | 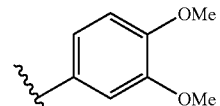 | NH₂ | 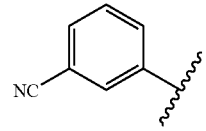 | 557 |
| 1078 | 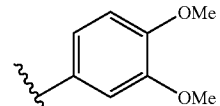 | NH₂ | 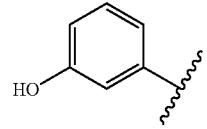 | 567 |
| 1079 | 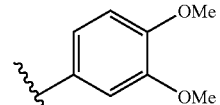 | NH₂ | 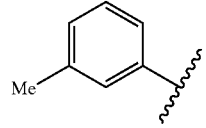 | 558 |
| 1080 | 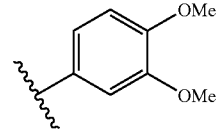 | NH₂ | | 556 |

TABLE 1-continued

| Cpd entry # | R¹ | R² | R³ | MS (MH)⁺ |
|---|---|---|---|---|
| 1081 | 3-(CF₃)-phenyl | NH₂ | 3,4-dimethoxyphenyl | 610 |
| 1082 | 3-F-phenyl | NH₂ | 3,4-dimethoxyphenyl | 560 |
| 1083 | 3,4-dimethylphenyl | NH₂ | 3,4-dimethoxyphenyl | 570 |
| 1084 | 4-(aminomethyl)phenyl | NH₂ | 3,4-dimethoxyphenyl | 585 |
| 1085 | 6-methoxypyridin-2-yl | NH₂ | 3,4-dimethoxyphenyl | 573 |
| 1086 | 6-fluoropyridin-3-yl | NH₂ | 3,4-dimethoxyphenyl | 561 |
| 1087 | 1H-indol-2-yl | NH₂ | 3,4-dimethoxyphenyl | 581 |
| 1088 | 6-(1H-pyrazol-1-yl)pyridin-2-yl | NH₂ | 3,4-dimethoxyphenyl | 609 |

TABLE 1-continued

| Cpd entry # | R¹ | R² | R³ | MS (MH)⁺ |
|---|---|---|---|---|
| 1089 | 6-(MeS)-pyridin-2-yl | NH₂ | 3,4-(OMe)₂-phenyl | 589 |
| 1090 | 4-Me-3-NO₂-phenyl | Br | 2-OEt-phenyl | 648/650 |
| 1091 | 4-Me-3-NO₂-phenyl | Br | 3-OEt-phenyl | 648/650 |
| 1092 | 4-Me-3-NO₂-phenyl | Br | 4-Br-phenyl | 682/684/686 |
| 1093 | 4-Me-3-NO₂-phenyl | Br | 3-MeO-4-OH-phenyl | 650/652 |
| 1094 | 4-Me-3-NO₂-phenyl | Br | 4-OMe-3-OH-phenyl | 650/652 |
| 1095 | 4-Me-3-NO₂-phenyl | Br | 2,4-(MeO)₂-phenyl | 664/666 |
| 1096 | 4-Me-3-NO₂-phenyl | Br | 2,6-(MeO)₂-phenyl | 664/666 |

TABLE 1-continued

| Cpd entry # | R¹ | R² | R³ | MS (MH)⁺ |
|---|---|---|---|---|
| 1097 | 4-Me, 3-NO₂-phenyl | Br | 2,4,6-triOMe-phenyl | 694/696 |
| 1098 | 4-Me, 3-NO₂-phenyl | Br | 3,4,5-triOMe-phenyl | 694/696 |
| 1099 | 4-Me, 3-NO₂-phenyl | Br | 2,3-diOMe-phenyl | 664/666 |
| 1100 | 4-Me, 3-NO₂-phenyl | Br | 2-Br-phenyl | 682/684/686 |
| 1101 | 4-Me, 3-NO₂-phenyl | Br | anthracen-9-yl | 704/706 |
| 1102 | 4-Me, 3-NO₂-phenyl | Br | naphthalen-1-yl | 654/656 |
| 1103 | 4-Me, 3-NO₂-phenyl | Br | 2-NO₂-phenyl | 649/651 |

TABLE 1-continued

| Cpd entry # | R¹ | R² | R³ | MS (MH)⁺ |
|---|---|---|---|---|
| 1104 | 4-Me-3-NO₂-phenyl | Br | 3-NO₂-phenyl | 649/651 |
| 1105 | 4-Me-3-NO₂-phenyl | Br | 3,4-diF-phenyl | 640/642 |
| 1106 | 4-Me-3-NO₂-phenyl | Br | 3-I-phenyl | 730/732 |
| 1107 | 4-Me-3-NO₂-phenyl | Br | 4-Et-phenyl | 632/634 |
| 1108 | 4-Me-3-NO₂-phenyl | Br | 3-CO₂Me-phenyl | 662/664 |
| 1109 | 4-Me-3-NO₂-phenyl | Br | 4-OMe-3-CF₃-phenyl | 702/704 |
| 1110 | 4-Me-3-NO₂-phenyl | Br | 2,4-diF-phenyl | 640/642 |
| 1111 | 4-Me-3-NO₂-phenyl | Br | 2,5-diF-phenyl | 640/642 |

TABLE 1-continued

| Cpd entry # | R¹ | R² | R³ | MS (MH)⁺ |
|---|---|---|---|---|
| 1112 | 4-Me-3-NO₂-phenyl | Br | 2,6-difluorophenyl | 640/642 |
| 1113 | 4-Me-3-NO₂-phenyl | Br | 2,5-dimethylphenyl | 632/634 |
| 1114 | 4-Me-3-NO₂-phenyl | Br | 3,5-dimethylphenyl | 632/634 |
| 1115 | 4-Me-3-NO₂-phenyl | Br | 2,3-difluorophenyl | 640/642 |
| 1116 | 4-Me-3-NO₂-phenyl | Br | 2-Cl-4-F-phenyl | 656/658/660 |
| 1117 | 4-Me-3-NO₂-phenyl | Br | 2-HO-4-OMe-phenyl | 650/652 |
| 1118 | 4-Me-3-NO₂-phenyl | Br | 2,4-dihydroxyphenyl | 636/638 |
| 1119 | 4-Me-3-NO₂-phenyl | Br | 2-MeS-phenyl | 650/652 |

TABLE 1-continued

| Cpd entry # | R¹ | R² | R³ | MS (MH)⁺ |
|---|---|---|---|---|
| 1120 | 4-Me-3-O₂N-phenyl | Br | 4-OH-phenyl | 620/622 |
| 1121 | 4-Me-3-O₂N-phenyl | Br | 4-OH-3-I-phenyl | 746/748 |
| 1122 | 4-Me-3-O₂N-phenyl | Br | 4-OH-3,5-diI-phenyl | 872/874 |
| 1123 | 4-Me-3-O₂N-phenyl | Br | 4-OMe-3-Me-phenyl | 648/650 |
| 1124 | 4-Me-3-O₂N-phenyl | Br | 4-OMe-2,3-diMe-phenyl | 662/664 |
| 1124 | 3-Me-4-O₂N-phenyl | Br | 4-Me-3-OMe-phenyl | 648/650 |
| 1125 | 4-Me-3-O₂N-phenyl | Br | phenyl | 604/606 |
| 1126 | 4-Me-3-O₂N-phenyl | Br | 1-Me-pyrrol-2-yl | 607/609 |

TABLE 1-continued

| Cpd entry # | R¹ | R² | R³ | MS (MH)⁺ |
|---|---|---|---|---|
| 1127 | 4-Me-3-NO₂-phenyl | Br | thiophen-3-yl | 610/612 |
| 1128 | 4-Me-3-NO₂-phenyl | Br | 1H-indol-3-yl | 643/645 |
| 1129 | 4-Me-3-NO₂-phenyl | Br | benzo[b]thiophen-3-yl | 660/662 |
| 1130 | 4-(aminoethyl)phenyl | NH₂ | 4-OH-3-OMe-phenyl | 571 |
| 1131 | 4-Me-3-N₃-phenyl | NH₂ | 4-OH-3-OMe-phenyl | 583 |
| 1132 | 3-NO₂-phenyl | H | 3,4-di-OMe-phenyl | 572 |

TABLE 2

| Cpd entry # | R¹ | R² | R⁴ R⁵ | R³ | MS (MH)⁺ |
|---|---|---|---|---|---|
| 2001 | 4-Me-3-NO₂-phenyl | H | C(Me)(Et) | 3,4-diOMe-phenyl | 600 |
| 2002 | 2-OMe-phenyl | H | cyclopropyl (spiro) | 3,4-diOMe-phenyl | 555 |
| 2003 | 2-OMe-phenyl | H | cyclopentyl (spiro) | 3,4-diOMe-phenyl | 583 |
| 2004 | 4-Me-3-NO₂-phenyl | H | cyclopentyl (spiro) | 3,4-diOMe-phenyl | 612 |
| 2005 | 4-Me-3-NO₂-phenyl | Br | cyclopentyl (spiro) | 3,4-diOMe-phenyl | 690/692 |
| 2006 | 4-Me-3-NO₂-phenyl | NH₂ | cyclopentyl (spiro) | 3,4-diOMe-phenyl | 627 |
| 2007 | 2-OMe-phenyl | H | cyclohexyl (spiro) | 3,4-diOMe-phenyl | 597 |

TABLE 2-continued

| Cpd entry # | R¹ | R² | R⁴ R⁵ | R³ | MS (MH)⁺ |
|---|---|---|---|---|---|
| 2008 | Me-, O₂N- phenyl | Br | cyclohexyl | 3,4-diOMe-phenyl | 704/706 |
| 2009 | Me-, O₂N- phenyl | NH₂ | cyclohexyl | 3,4-diOMe-phenyl | 641 |
| 2010 | Me-, O₂N- phenyl | NH₂ | cyclohexyl | 4-OH, 3-OMe-phenyl | 627 |
| 2011 | Me-pyridyl | NH₂ | cyclohexyl | 3,4-diOMe-phenyl | 597 |

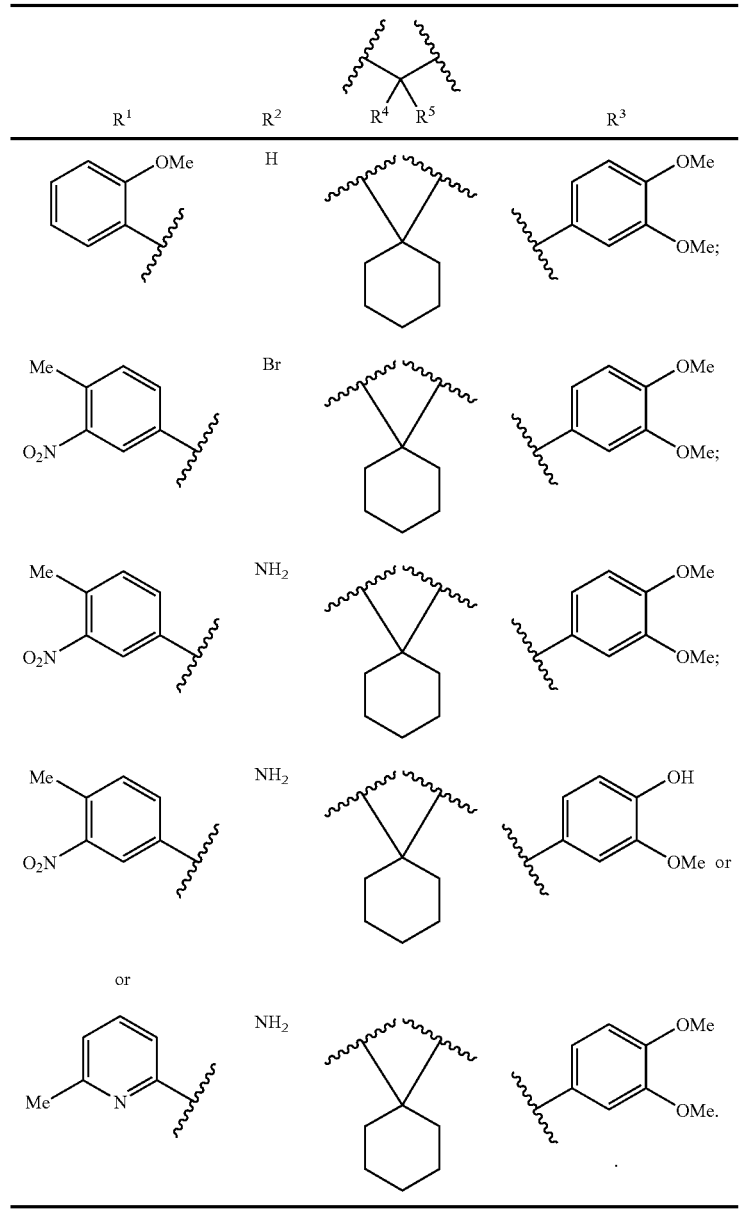

What is claimed is:

1. A compound of formula (Ia), or an enantiomer or a salt thereof:

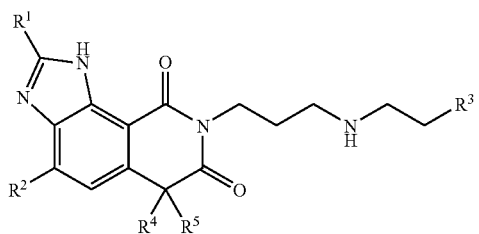

(Ia)

wherein R¹ is —(CH=CH)$_{0-1}$—(C$_6$ or C$_{10}$)aryl or —(CH=CH)$_{0-1}$-5-, 6-, 9- or 10-membered heteroaryl, said aryl or heteroaryl being optionally substituted with one, two or three substituents, each independently selected from:

(C$_{1-6}$)alkyl optionally substituted with amino, halo, (C$_{1-6}$)haloalkyl, hydroxy, (C$_{1-6}$)alkoxy, (C$_{1-6}$)alkylthio, nitro, azido, cyano, amino, (C$_{1-6}$)alkylamino, di((C$_{1-6}$)alkyl)amino, aryl and heteroaryl;

R² is H, (C$_{1-6}$)alkyl, hydroxy, halo, (C$_{1-6}$)haloalkyl, amino, (C$_{1-6}$)alkylamino, di((C$_{1-6}$)alkyl)amino, or (C$_{2-6}$)alkynyl;

R³ is (C$_6$, C$_{10}$ or C$_{14}$)aryl or 5-, 6-, 9- or 10-membered heteroaryl, each of which being optionally substituted-with one, two or three substituents, each independently selected from:

(C$_{1-6}$)alkyl, halo, (C$_{1-6}$)haloalkyl, hydroxy, (C$_{1-6}$)alkoxy, (C$_{1-6}$)alkylthio, nitro, amino, (C$_{1-6}$)alkylamino, di((C$_{1-6}$)alkyl)amino and COO(C$_{1-6}$)alkyl; and R$^4$ and R$^5$ are each independently H or (C$_{1-6}$)alkyl; or R$^4$ and R$^5$ are linked, together with the carbon atom to which they are attached, to form a (C$_{3-7}$)cycloalkyl group;

with the proviso that R$^1$ is not 2-methoxyphenyl, when R$^2$ is H, R$^3$ is 3,4-dimethoxyphenyl, R$^4$ is CH$_3$ and R$^5$ is CH$_3$.

2. The compound according to claim 1 wherein
R$^1$ is —(CH=CH)$_{0-1}$—(C$_6$ or C$_{10}$)aryl or 5-, 6-, 9- or 10-membered heteroaryl, said aryl or heteroaryl being optionally substituted with one, two or three substituents, each independently selected from:
(C$_{1-6}$)alkyl optionally substituted with amino, halo, (C$_{1-6}$)haloalkyl, hydroxy, (C$_{1-6}$)alkoxy, (C$_{1-6}$)alkylthio, nitro, azido, cyano, amino, (C$_{1-6}$)alkylamino, di((C$_{1-6}$)alkyl)amino, aryl and heteroaryl;
R$^2$ is H, (C$_{1-6}$)alkyl, hydroxy, halo, (C$_{1-6}$)haloalkyl, amino, (C$_{1-6}$)alkylamino, di((C$_{1-6}$)alkyl)amino, or (C$_{2-6}$)alkynyl;
R$^3$ is (C$_6$, C$_{10}$ or C$_{14}$)aryl or 5-, 6-, 9- or 10-membered heteroaryl, each of which being optionally substituted with one, two or three substituents, each independently selected from:
(C$_{1-6}$)alkyl, halo, (C$_{1-6}$)haloalkyl, hydroxy, (C$_{1-6}$)alkoxy, (C$_{1-6}$)alkylthio, amino, (C$_{1-6}$)alkylamino and di((C$_{1-6}$)alkyl)amino; and
R$^4$ and R$^5$ are each independently (C$_{1-6}$)alkyl; or R$^4$ and R$^5$ are linked, together with the carbon atom to which they are attached, to form a (C$_{3-7}$)cycloalkyl group;
with the proviso that R$^1$ is not 2-methoxyphenyl, when R$^2$ is H, R$^3$ is 3,4-dimethoxyphenyl, R$^4$ is CH$_3$ and R$^5$ is CH$_3$.

3. The compound according to claim 1 wherein:
R$^1$ is (CH=CH)$_{0-1}$-phenyl, the phenyl being optionally substituted with one, two or three substituents, each independently selected from:
(C$_{1-6}$)alkyl optionally substituted with amino, halo, (C$_{1-6}$)haloalkyl, hydroxy, (C$_{1-6}$)alkoxy, (C$_{1-6}$)alkylthio, amino, nitro, cyano, azido, (C$_{1-6}$)alkylamino, di((C$_{1-6}$)alkyl)amino, and heteroaryl;
or R$^1$ is a 5-, 6-, 9- or 10-membered heteroaryl optionally substituted with one, two or three substituents, each independently selected from nitro, (C$_{1-6}$)alkyl optionally substituted with amino, (C$_{1-6}$)haloalkyl, hydroxy, (C$_{1-6}$)alkoxy, halo, (C$_{1-6}$)alkylthio, cyano and heteroaryl;
R$^2$ is H, (C$_{1-6}$)alkyl, hydroxy, halo, amino, (C$_{1-6}$)alkylamino, or (C$_{2-6}$)alkynyl;
R$^3$ is naphthyl, anthryl, or phenyl optionally substituted with one, two or three substituents, each independently selected from:
(C$_{1-6}$)alkyl, halo, (C$_{1-6}$)haloalkyl, hydroxy, (C$_{1-6}$)alkoxy, and (C$_{1-6}$)alkylthio;
or R$^3$ is a 5-, 6-, 9- or 10-membered heteroaryl optionally substituted with (C$_{1-6}$)alkyl; and
R$^4$ and R$^5$ are each independently Me or Et; or R$^4$ and R$^5$ are linked, together with the carbon atom to which they are attached, to form a (C$_{3-7}$)cycloalkyl group;
with the proviso that R$^1$ is not 2-methoxyphenyl, when R$^2$ is H, R$^3$ is 3,4-dimethoxyphenyl, R$^4$ is CH$_3$ and R$^5$ is CH$_3$.

4. The compound according to claim 1 wherein:
R$^1$ is phenyl, 2-pyridyl, quinolinyl or benzofuranyl, the phenyl and 2-pyridyl each being optionally substituted with one or two substituents, each independently selected from:
methyl, hydroxy, methoxy, nitro, cyano, methylthio, fluoro, 2-aminoethyl and CF$_3$;
R$^2$ is H, NH$_2$, bromo, chloro, or OH;
R$^3$ is naphthyl, or phenyl optionally substituted with one, two or three substituents, each independently selected from:
methyl, iodo, hydroxy, methoxy, ethoxy and methylthio; and
R$^4$ and R$^5$ are each independently Me; or R$^4$ and R$^5$ are linked, together with the carbon atom to which they are attached, to form a cyclopentyl or cyclohexyl group;
with the proviso that R$^1$ is not 2-methoxyphenyl, when R$^2$ is H, R$^3$ is 3,4-dimethoxyphenyl, R$^4$ is CH$_3$ and R$^5$ is CH$_3$.

5. The compound according to claim 1 wherein:
R$^1$ is phenyl, 2-pyridyl, quinolinyl or benzofuranyl, the phenyl and 2-pyridyl each being optionally substituted with one or two substituents, each independently selected from:
methyl, methoxy, fluoro, CF$_3$, nitro, cyano, and methylthio;
R$^2$ is H, NH$_2$, bromo, chloro, or OH;
R$^3$ is phenyl optionally substituted with one, two or three substituents, each independently selected from:
hydroxy, methoxy, ethoxy, methyl, iodo and methylthio; and
R$^4$ and R$^5$ are each independently Me; or R$^4$ and R$^5$ are linked, together with the carbon atom to which they are attached, to form a cyclopentyl or cyclohexyl group;
with the proviso that R$^1$ is not 2-methoxyphenyl, when R$^2$ is H, R$^3$ is 3,4-dimethoxyphenyl, R$^4$ is CH$_3$ and R$^5$ is CH$_3$.

6. The compound according to claim 1 wherein:
R$^1$ is

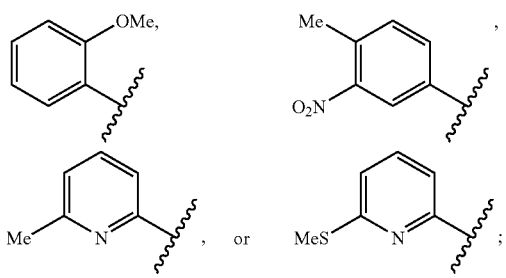

R$^2$ is NH$_2$ or bromo;
R$^3$ is phenyl substituted with one or two substituents each independently selected from hydroxy, methoxy, and iodo; and
R$^4$ and R$^5$ are each independently Me; or R$^4$ and R$^5$ are linked, together with the carbon atom to which they are attached, to form a cyclohexyl group.

7. The compound according to claim 1, or an enantiomer or salt thereof, of the formula:

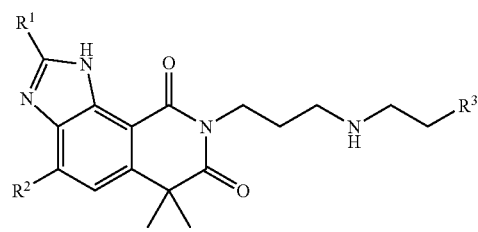

wherein R¹, R² and R³ are defined as in the table below:

| Cpd entry # | R¹ | R² | R³ |
|---|---|---|---|
| 1002 | 3-NC-C₆H₄- | H | 3,4-(OMe)₂-C₆H₃- |
| 1003 | 3-F-C₆H₄- | H | 3,4-(OMe)₂-C₆H₃- |
| 1004 | 4-HO-C₆H₄- | H | 3,4-(OMe)₂-C₆H₃- |
| 1005 | 3-F₃C-C₆H₄- | H | 3,4-(OMe)₂-C₆H₃- |
| 1006 | 3-Me-C₆H₄- | H | 3,4-(OMe)₂-C₆H₃- |
| 1007 | 4-Cl-3-O₂N-C₆H₃- | H | 3,4-(OMe)₂-C₆H₃- |
| 1008 | 4-HO-3-Me-C₆H₃- | H | 3,4-(OMe)₂-C₆H₃- |
| 1009 | 4-Me-3-O₂N-C₆H₃- | H | 3,4-(OMe)₂-C₆H₃- |
| 1010 | 4-Cl-3-F-C₆H₃- | H | 3,4-(OMe)₂-C₆H₃- |
| 1011 | 3-Cl-C₆H₄- | H | 3,4-(OMe)₂-C₆H₃- |

-continued

| Cpd entry # | R¹ | R² | R³ |
|---|---|---|---|
| 1012 | 4-F, 3-Cl-phenyl | H | 3,4-diOMe-phenyl |
| 1013 | benzo[1,3]dioxol-4-yl | H | 3,4-diOMe-phenyl |
| 1014 | 4-O₂N-phenyl | H | 3,4-diOMe-phenyl |
| 1015 | 2,3-diCl-phenyl | H | 3,4-diOMe-phenyl |
| 1016 | 3,4-diMe-phenyl | H | 3,4-diOMe-phenyl |
| 1017 | 4-MeO, 3-O₂N-phenyl | H | 3,4-diOMe-phenyl |
| 1018 | 3-F, 2-OMe-phenyl | H | 3,4-diOMe-phenyl |
| 1019 | 4-Me₂N, 3-O₂N-phenyl | H | 3,4-diOMe-phenyl |
| 1020 | 4-HO, 3-O₂N-phenyl | H | 3,4-diOMe-phenyl |

-continued
| Cpd entry # | R¹ | R² | R³ |
|---|---|---|---|
| 1021 | 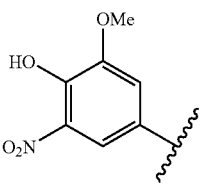 | H | 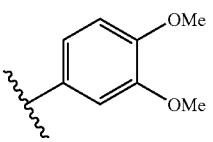 |
| 1022 | 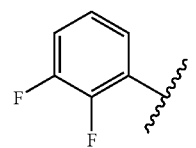 | H | 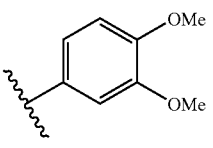 |
| 1023 | 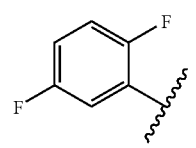 | H | 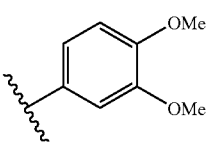 |
| 1024 | 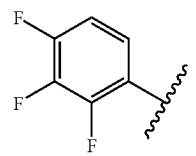 | H | 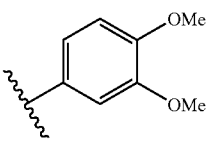 |
| 1025 | 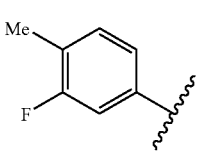 | H | 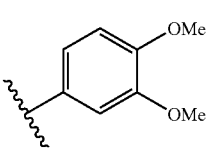 |
| 1026 | 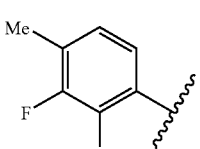 | H | 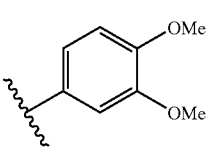 |
| 1027 | 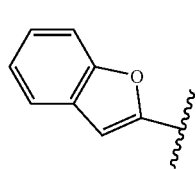 | H | 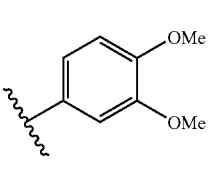 |
| 1028 | 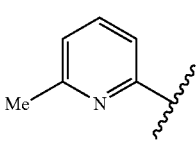 | H | 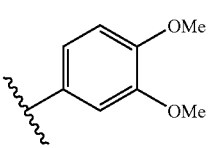 |
| 1029 | 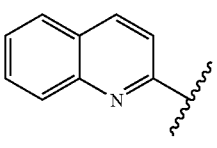 | H | 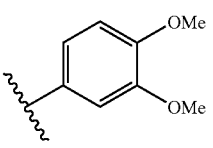 |

-continued

| Cpd entry # | R¹ | R² | R³ |
|---|---|---|---|
| 1030 | 8-hydroxyquinolin-2-yl | H | 3,4-dimethoxyphenyl |
| 1031 | 5-chloro-1H-indol-3-yl | H | 3,4-dimethoxyphenyl |
| 1032 | 5-nitrofuran-2-yl | H | 3,4-dimethoxyphenyl |
| 1033 | 1H-indol-2-yl | H | 3,4-dimethoxyphenyl |
| 1034 | quinolin-3-yl | H | 3,4-dimethoxyphenyl |
| 1035 | quinoxalin-2-yl | H | 3,4-dimethoxyphenyl |
| 1036 | quinolin-6-yl | H | 3,4-dimethoxyphenyl |
| 1037 | 2-nitrothiophen-4-yl | H | 3,4-dimethoxyphenyl |
| 1038 | 5-nitro-1H-pyrrol-2-yl | H | 3,4-dimethoxyphenyl |

-continued
| Cpd entry # | R¹ | R² | R³ |
|---|---|---|---|
| 1039 | 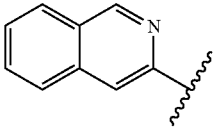 | H | 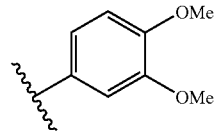 |
| 1040 | 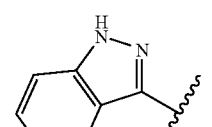 | H | 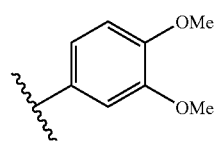 |
| 1041 | 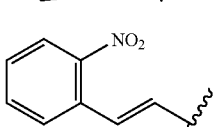 | H | 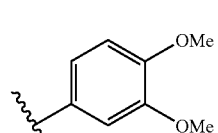 |
| 1042 | 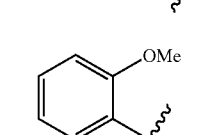 | H | 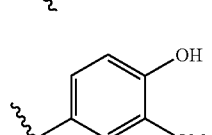 |
| 1043 | 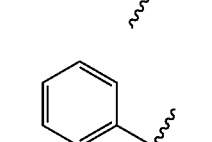 | H | 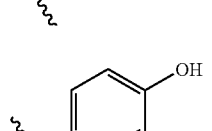 |
| 1044 | 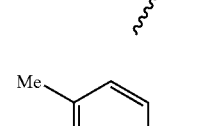 | H | 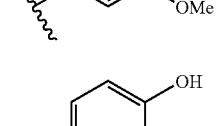 |
| 1045 | 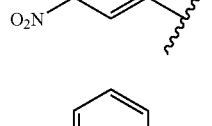 | H | 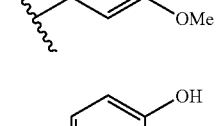 |
| 1046 | 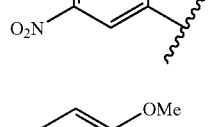 | Br | 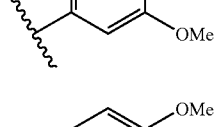 |
| 1047 | 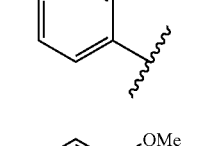 | Et | 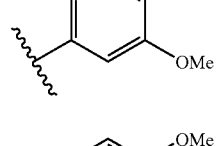 |
| 1048 | 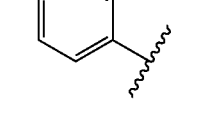 | NH₂ | 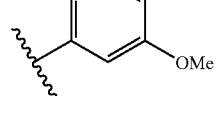 |

-continued

| Cpd entry # | R¹ | R² | R³ |
|---|---|---|---|
| 1049 | 2-OMe-phenyl | C≡CH | 3,4-di-OMe-phenyl |
| 1050 | 2-OMe-phenyl | NHMe | 3,4-di-OMe-phenyl |
| 1051 | 2-OMe-phenyl | Me | 3,4-di-OMe-phenyl |
| 1052 | phenyl | Br | 3,4-di-OMe-phenyl |
| 1053 | 4-Me-3-NO₂-phenyl | Br | 3,4-di-OMe-phenyl |
| 1054 | 4-Me-3-NO₂-phenyl | Cl | 3,4-di-OMe-phenyl |
| 1055 | 4-Me-3-NO₂-phenyl | OH | 3,4-di-OMe-phenyl |
| 1056 | 2-OMe-phenyl | Br | 4-OH-3-OMe-phenyl |
| 1057 | 4-Me-3-NO₂-phenyl | Br | 4-OH-3-OMe-phenyl |
| 1058 | 4-Me-3-NO₂-phenyl | NH₂ | 4-OH-3-OMe-phenyl |

-continued

| Cpd entry # | R¹ | R² | R³ |
|---|---|---|---|
| 1059 | 4-Me-3-nitrophenyl | NH₂ | 3,4-dimethoxyphenyl |
| 1060 | quinolin-2-yl | Br | 3,4-dimethoxyphenyl |
| 1061 | benzofuran-2-yl | Br | 3,4-dimethoxyphenyl |
| 1062 | 6-methylpyridin-2-yl | Br | 3,4-dimethoxyphenyl |
| 1063 | 3-cyanophenyl | Br | 3,4-dimethoxyphenyl |
| 1064 | 3-methylphenyl | Br | 3,4-dimethoxyphenyl |
| 1065 | 3-(trifluoromethyl)phenyl | Br | 3,4-dimethoxyphenyl |
| 1066 | 3-fluorophenyl | Br | 3,4-dimethoxyphenyl |
| 1067 | 3,4-dimethylphenyl | Br | 3,4-dimethoxyphenyl |
| 1068 | 2-methyl-1H-imidazol-4-yl | Br | 3,4-dimethoxyphenyl |

-continued
| Cpd entry # | R¹ | R² | R³ |
|---|---|---|---|
| 1069 |  | Br |  |
| 1070 |  | Br |  |
| 1071 |  | Br |  |
| 1072 |  | Br |  |
| 1073 |  | Br |  |
| 1074 |  | Br |  |
| 1075 |  | NH₂ |  |
| 1076 |  | NH₂ |  |
| 1077 |  | NH₂ |  |
| 1078 |  | NH₂ |  |

-continued

| Cpd entry # | R¹ | R² | R³ |
|---|---|---|---|
| 1079 | 3-hydroxyphenyl | NH₂ | 3,4-dimethoxyphenyl |
| 1080 | 3-methylphenyl | NH₂ | 3,4-dimethoxyphenyl |
| 1081 | 3-(trifluoromethyl)phenyl | NH₂ | 3,4-dimethoxyphenyl |
| 1082 | 3-fluorophenyl | NH₂ | 3,4-dimethoxyphenyl |
| 1083 | 3,4-dimethylphenyl | NH₂ | 3,4-dimethoxyphenyl |
| 1084 | 4-(2-aminoethyl)phenyl | NH₂ | 3,4-dimethoxyphenyl |
| 1085 | 6-methoxypyridin-2-yl | NH₂ | 3,4-dimethoxyphenyl |
| 1086 | 6-fluoropyridin-2-yl | NH₂ | 3,4-dimethoxyphenyl |
| 1087 | 1H-indol-2-yl | NH₂ | 3,4-dimethoxyphenyl |
| 1088 | 6-(1H-pyrazol-1-yl)pyridin-2-yl | NH₂ | 3,4-dimethoxyphenyl |

-continued
| Cpd entry # | R¹ | R² | R³ |
|---|---|---|---|
| 1089 | 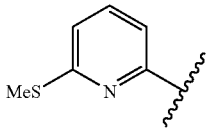 | NH₂ | 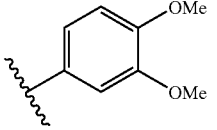 |
| 1090 | 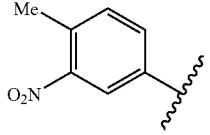 | Br | 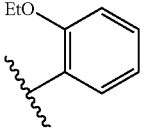 |
| 1091 | 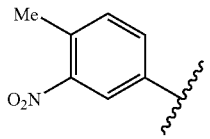 | Br | 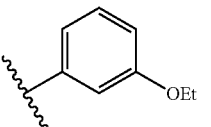 |
| 1092 | 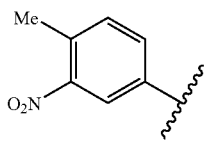 | Br | 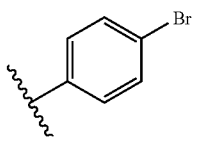 |
| 1093 | 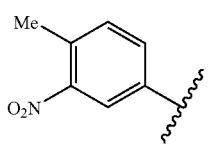 | Br | 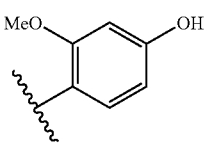 |
| 1094 | 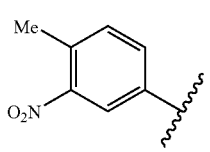 | Br | 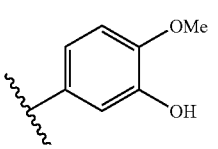 |
| 1095 | 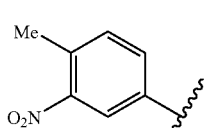 | Br | 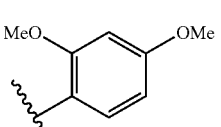 |
| 1096 | 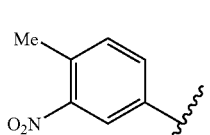 | Br | 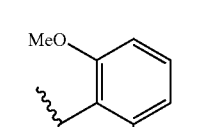 |
| 1097 | 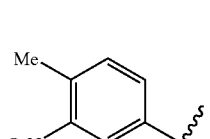 | Br | 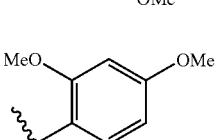 |

-continued

| Cpd entry # | R¹ | R² | R³ |
|---|---|---|---|
| 1098 | 4-Me-3-O₂N-C₆H₃- | Br | 3,4,5-(MeO)₃-C₆H₂- |
| 1099 | 4-Me-3-O₂N-C₆H₃- | Br | 2,3-(MeO)₂-C₆H₃- |
| 1100 | 4-Me-3-O₂N-C₆H₃- | Br | 2-Br-C₆H₄- |
| 1101 | 4-Me-3-O₂N-C₆H₃- | Br | anthracen-9-yl |
| 1102 | 4-Me-3-O₂N-C₆H₃- | Br | naphthalen-1-yl |
| 1103 | 4-Me-3-O₂N-C₆H₃- | Br | 2-O₂N-C₆H₄- |
| 1104 | 4-Me-3-O₂N-C₆H₃- | Br | 3-O₂N-C₆H₄- |
| 1105 | 4-Me-3-O₂N-C₆H₃- | Br | 3,4-F₂-C₆H₃- |
| 1106 | 4-Me-3-O₂N-C₆H₃- | Br | 3-I-C₆H₄- |

-continued
| Cpd entry # | R¹ | R² | R³ |
|---|---|---|---|
| 1107 | 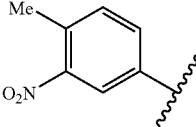 | Br | 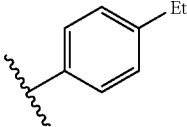 |
| 1108 | 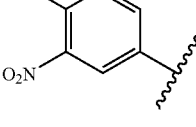 | Br | 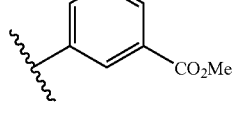 |
| 1109 | 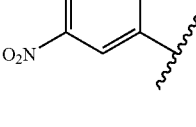 | Br | 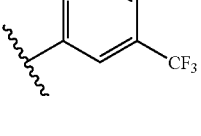 |
| 1110 | 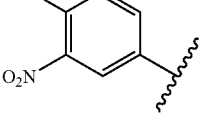 | Br | 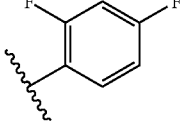 |
| 1111 | 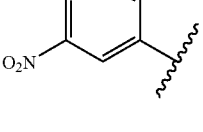 | Br | 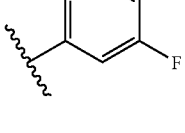 |
| 1112 | 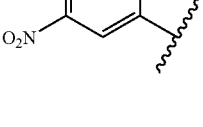 | Br | 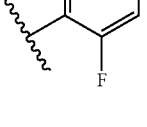 |
| 1113 | 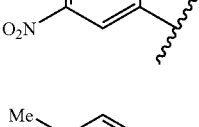 | Br | 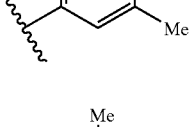 |
| 1114 | 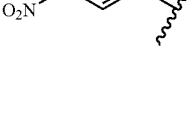 | Br | 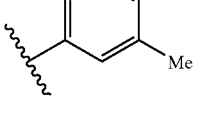 |
| 1115 | 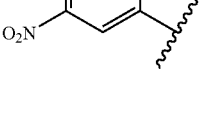 | Br | 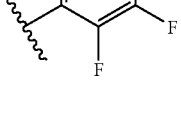 |

-continued
| Cpd entry # | R¹ | R² | R³ |
|---|---|---|---|
| 1116 | 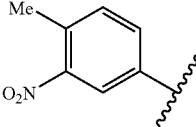 | Br | 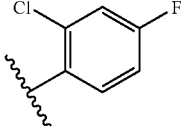 |
| 1117 | 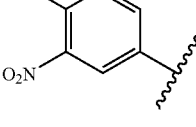 | Br | 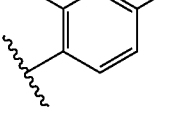 |
| 1118 | 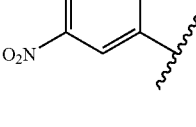 | Br | 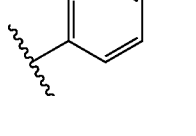 |
| 1119 | 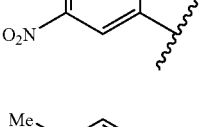 | Br | 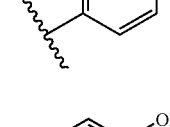 |
| 1120 | 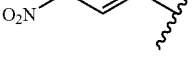 | Br | 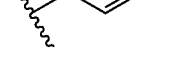 |
| 1121 | 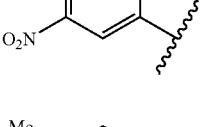 | Br | 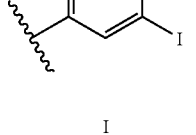 |
| 1122 | 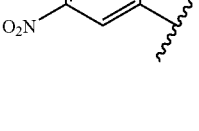 | Br | 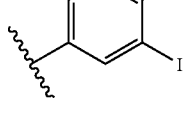 |
| 1123 | 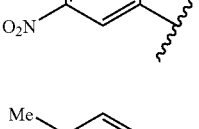 | Br | 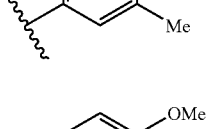 |
| 1124 | 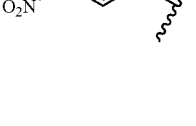 | Br | 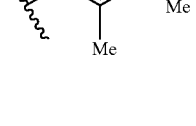 |

-continued
| Cpd entry # | R¹ | R² | R³ |
|---|---|---|---|
| 1124 | 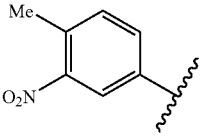 | Br | 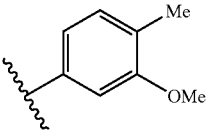 |
| 1125 | 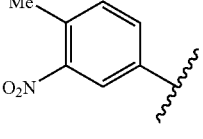 | Br | 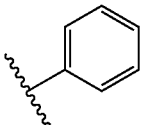 |
| 1126 | 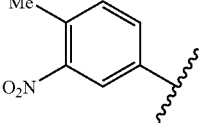 | Br | 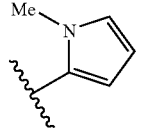 |
| 1127 | 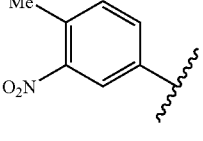 | Br | 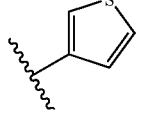 |
| 1128 | 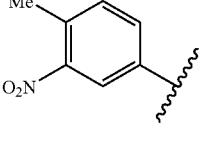 | Br | 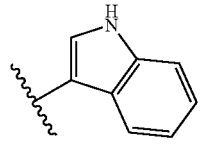 |
| 1129 | 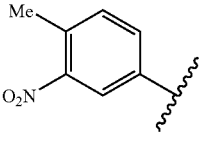 | Br | 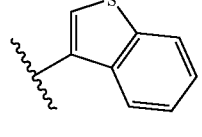 |
| 1130 | 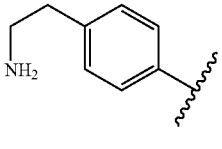 | NH₂ | 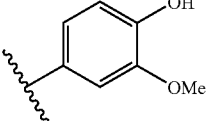 |
| 1131 | 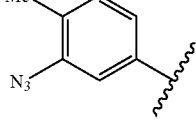 | NH₂ | 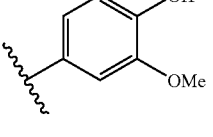 |
| or | | | |
| 1132 | 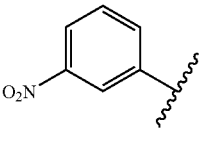 | H | 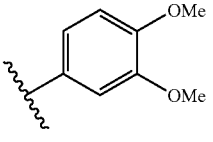 |

8. The compound according to claim 1, or an enantiomer or salt thereof, of the formula:
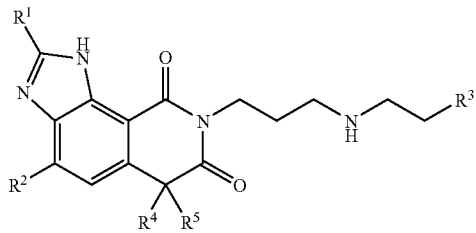
wherein $R^1$, $R^2$, $R^3$, $R^4$ and $R^5$ are defined as in the table below: